US006730503B1

(12) United States Patent
Asakura et al.

(10) Patent No.: US 6,730,503 B1
(45) Date of Patent: May 4, 2004

(54) ALCOHOL/ALDEHYDE DEHYDROGENASE

(75) Inventors: Akira Asakura, Fujisawa (JP); Tatsuo Hoshino, Kamakura (JP); Setsuko Ojima, Fujisawa (JP); Masako Shinjoh, Kamakura (JP); Noribumi Tomiyama, Fujisawa (JP)

(73) Assignee: Roche Vitamins Inc., Parsippany, NJ (US)

( * ) Notice: Subject to any disclaimer, the term of this patent is extended or adjusted under 35 U.S.C. 154(b) by 0 days.

(21) Appl. No.: 09/470,667

(22) Filed: Dec. 22, 1999

Related U.S. Application Data

(63) Continuation of application No. 08/934,506, filed on Sep. 19, 1997, now abandoned.

(30) Foreign Application Priority Data

Sep. 19, 1996 (EP) .............................. 96115001

(51) Int. Cl.⁷ .............................. C12P 7/40; C12P 7/60; C12P 7/24; C12P 7/26; C12N 9/04
(52) U.S. Cl. ........................ 435/136; 435/41; 435/138; 435/147; 435/148; 435/252.33; 435/252.34; 435/320.1; 435/69.2; 435/190; 435/419; 435/252.3; 536/23.2
(58) Field of Search ................................ 435/138, 136, 435/148, 41, 320.1, 252.3, 190; 536/23.2

(56) References Cited

U.S. PATENT DOCUMENTS

| 3,234,105 A | 2/1966 | Motizuki et al. |
| 3,912,592 A | 10/1975 | Makover et al. |
| 4,960,695 A | 10/1990 | Hoshino et al. |
| 5,352,599 A | 10/1994 | Fujiwara et al. |
| 5,437,989 A | 8/1995 | Asakura et al. |
| 5,541,108 A | 7/1996 | Fujiwara et al. |

FOREIGN PATENT DOCUMENTS

| EP | 0 221 707 | 5/1987 |
| EP | 0 278 447 | 8/1988 |
| EP | 0 366 922 | 5/1990 |
| EP | 0 448 969 A2 | 10/1991 |
| EP | 0 606 621 | 7/1994 |
| EP | 0 645 453 | 3/1995 |
| JP | 51-40154 | 11/1976 |

OTHER PUBLICATIONS

Zizheng, et al., "Studies on Production of Vitamin C Precursor 2–Keto–L–Gulonic Acid from L–Sorbose by Fermentation," *Acta Microbiologica Sinica*, 21(2), 185–191 (1981).
English language Abstract of JP 51–40154 (document B1).
Rudinger, "Characteristics of the amino acids as components of a peptide hormone sequence," In *Peptide Hormones*, Ed. J.A. Parsons, University Park Press, Baltimore, MD, pp. 1–7 (1976).

Ngo, et al., "Computational complexity, protein structure prediction, and the ILevinthal paradox, "In: *The Protein Folding Problem and Tertiary Structure Prediction*, Eds. Merz, et al., Boston, MA, pp. 491–495 (1994).
Thornton, et al., "Protein Engineering: Editorial Overview," *Current Opinion In Biotechnology*, 6(4): 367–369 (1995).
Wallace, "Understanding cytochrome c function: engineering protein structure by semisynthesis," *The FASEB Journal*, 7: 505–515 (1993).
Maniatis, et al., Chapter 12: "Vectors that express cloned DNA in *Escherichia coli*," In *Molecular Cloning: A Laboratory Manual*, Cold Spring Harbour Laboratory Press, pp. 404–433 (1982).
Matsudira, "Limited N–terminal sequence analysis," *Methods in Enzymology*, vol. 182, pp. 602–613 (1991).
Wozney, "Using purified protein to clone its gene," *Methods in Enzymology*, 182: 738–751 (1991).
Stoorvage, et al., "Characterization of the gene encoding quinohaemoprotein ethanol dehydrogenase of *Comamonas testosteroni*," *Eur. J. Biochem.*, 235: 690–698 (1996).
"Alcohol dehydrogenase complex structural gene–used in plasmid and enhancing efficiency of acetic acid fermentation for transformed acetic acid bacteria," GENESEQ DATABASE, Accession No. R20192 (1992).
Tamaki, et al., "Cloning and sequencing of the gene cluster encoding two subunits of membrane–bound alcohol dehydrogenase from *Acetobacter polyoxogenes*," *Biochim. Biophys. Acta*, 1088: 292–300 (1991).
Kondo, K. and Horinouchi, S., "Characterization of the Genes Encoding the Three–Component Membrane–Bound Alcohol Dehydrogenase from *Gluconobacter suboxydans* and Their Expression in *Acetobacter pasteurianus*," *Applied and Environmental Microbiology*, 63(3): 1131–138 (1997).
Reid, M.F. and Fewson, C., "Molecular Characterization of Microbial Alcohol Dehydrogenases," *Crit. Rev. Microbiol.*, 20(1): 13–56 (1994).

Primary Examiner—Rebecca E. Prouty
Assistant Examiner—Malgorzata A. Walicka
(74) Attorney, Agent, or Firm—Bryan Cave LLP

(57) ABSTRACT

The present invention is directed to a recombinant enzymes having alcohol and aldehyde dehydrogenase activity which comprises one or mom recombinant polypeptides selected from the group consisting of polypeptides which are identified by SEQ ID NO 5, SEQ ID NO 6, SEQ ID NO 7, SEQ ID NO 8 and chimeric recombinant polypeptides that are a chimeric combination of at least two of the following amino acid sequences identified by SEQ ID NO 5, SEQ ID NO 6, SEQ ID NO 7, SEQ ID NO 8 and functional derivatives of the polypeptides identified above which contain addition, insertion, deletion and/or substitution of one or more amino acid residues, wherein said enzymatic polypeptides have said alcohol and aldehyde dehydrogenase activity. DNA molecules encoding the recombinant polypeptides, vectors comprising such DNA molecules, host cells transformed by such vectors and processes for the production of such recombinant enzymes are provided. Furthermore the recombinant enzymes having alcohol and aldehyde dehydrogenase activity are used for obtaining aldehydes, ketones or carboxylic acids, and specifically, 2-keto-L-gulonic acid an intermediate for the production of L-ascorbic acid (vitamin C).

26 Claims, 9 Drawing Sheets pSSAB201
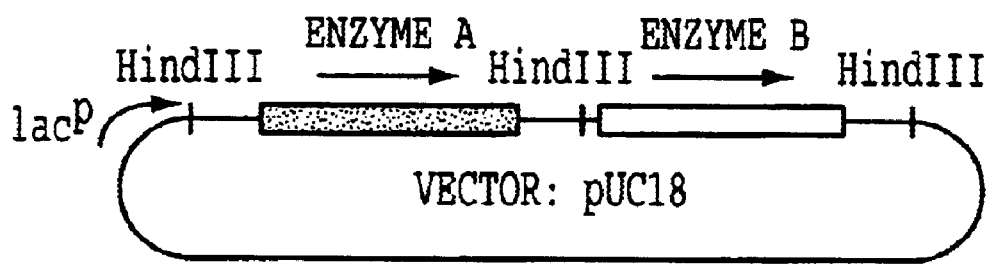
pSSBA201
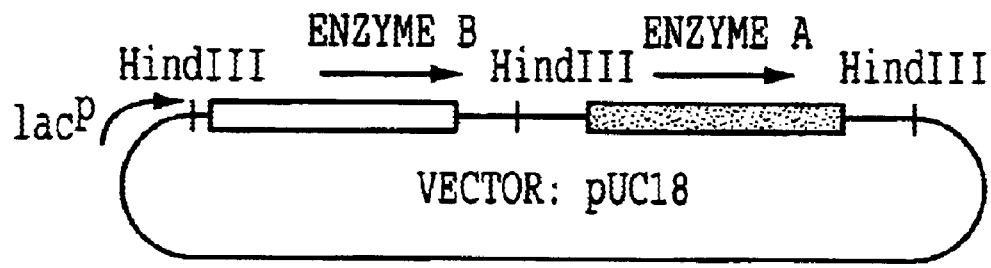
FIG. 3

RECOMBINATION SITE

*1 : AMINO ACID RESIDUE NO. 135 OF MATURE ENZYME A

*2 : AMINO ACID RESIDUE NO. 128 OF MATURE ENZYME A

*3 : AMINO ACID RESIDUE NO. 125 OF MATURE ENZYME A

*4 : AMINO ACID RESIDUE NO. 95 OF MATURE ENZYME A

*5 : AMINO ACID RESIDUE NO. 180 OF MATURE ENZYME B, WHICH NUCLEOTIDE SEQUENCE OF AvaI SITE ENCODES

```
ENZYME A   1 : QVTPVTDELL ANPPAGEWIS YGQNQENYRH SPLTQITTEN VGQLQLVWAR GMQPGKVQVT
               **** ***** ********* ** ******* ****** * ********** ** * ****
ENZYME B   1 : QVTPITDELL ANPPAGEWIN YGRNQENYRH SPLTQITADN VGQLQLVWAR GMEAGAVQVT

61 : PLIHDGVMYL ANPGDVIQAI DAKTGDLIWE HRRQLPNIAT LNSFGEPTRG MALYGTNVYF
               * ******** ********* ** ******* ****** ** ** *  ** ***** **
          61 : PMIHDGVMYL ANPGDVIQAL DAQTGDLIWE HRRQLPAVAT LNAQGDRKRG VALYGTSLYF
                                                                                    *
                                                                                   AvaI
         121 : VSWDNHLVAL DTATGQVTFD VDRGQGED-M VSNSSGPIVA NGVIVAGSTC QYSPFGCFVS
               ****** ** * **** ** * ** ***    ** ***** ********** **** *** *
         121 : SSWDNHLIAL DMETGQVVFD VERGSGEDGL TSNTTGPIVA NGVIVAGSTC QYSPYGCFIS

180 : GHDSATGEEL WRNYFIPRAG EEGDETWGND YEARWMTGAW GQITYDPVTN LVHYGSTAVG
               ********** *** ***  * ********** ******* * ********** ** **** **
         181 : GHDSATGEEL WRNHFIPQPG EEGDETWGND FEARWMTGVW GQITYDPVTN LVFYGSTGVG

240 : PASETQRGTP GGTLYGTNTR FAVRPDTGEI VWRHQTLPRD NWDQECTFEM MVTNVDVQPS
               ********** ********** ********** ********** ********** ** *******
         241 : PASETQRGTP GGTLYGTNTR FAVRPDTGEI VWRHQTLPRD NWDQECTFEM MVANVDVQPS
                                                                           *
                                                                         EcoRI
         300 : TEMEGLQSIN PNAATGERRV LTGVPCKTGT MWQFDAETGE FLWARDTNYQ NMIESIDENG
               ***** ** ********** *** ****** ** *** ** ********* *** **** *
         301 : AEMEGLRAIN PNAATGERRV LTGAPCKTGT MWSFDAASGE FLWARDTNYT NMIASIDETG

360 : IVTVNEDAIL KELDVEYDVC PTFLGGRDWP SAALNPDSGI YFIPLNNVCY DMMAVDQEFT
               ****** * ********** ********  ****** ** ** **** ** * *******
         361 : LVTVNEDAVL KELDVEYDVC PTFLGGRDWS SAALNPDTGI YFLPLNNACY DIMAVDQEFS
                                                                              *
                                                                            SalI
         420 : SMDVYNTSNV TKLPPGKDMI GRIDAIDIST GRTLWSVERA AANYSPVLST GGGVLFNGGT
               ******      ** ** ********** ****** ** ********** *** *****
         421 : ALDVYNTSAT AKLAPGFENM GRIDAIDIST GRTLWSAERP AANYSPVLST AGGVVFNGGT

480 : DRYFRALSQE TGETLWQTRL ATVASGQAIS YEVDGMQYVA IAGGGVSYGS GLNSALAGER
               ********** ****** ** **** ***** ** ** ** *  ** **  ** ** *
         481 : DRYFRALSQE TGETLWQARL ATVATGQAIS YELDGVQYIA IGAGGLTYGT QLNAPLA-EA

540 : VDSTAIGNAV YVFALPQ
               *** *** ******
         540 : IDSTSVGNAI YVFALPQ

* : NUCLEOTIDE SEQUENCES ENCODING THESE REGIONS ARE THE RESTRICTION SITES
    FOR AvaI, EcoRI, AND SalI WHICH WERE USED FOR CONSTRUCTING CHIMERA
    GENES SHOWN IN FIG. 2.
```

FIG. 5

*: AvaI, EcoRI, SalI SITES USED FOR CONSTRUCTING CHIMERA GENES SHOWN IN FIG. 2 AND 6.

SEQUENCE LISTING

```
<160> NUMBER OF SEQ ID NOS: 12

<210> SEQ ID NO 1
<211> LENGTH: 1740
<212> TYPE: DNA
<213> ORGANISM: Gluconobacter oxydans

<400> SEQUENCE: 1
atgaaaccga cttcgctgct ttgggccagt gctggcgcac ttgcattgct tgccgcaccc       60
gcctttgctc aagtgacccc cgtcaccgat gaattgctgg cgaacccgcc cgctggtgaa      120
tggatcagct acggtcagaa ccaagaaaac taccgtcact cgcccctgac gcagatcacg      180
actgagaacg tcgccaact gcaactggtc tgggcgcgcg gcatgcagcc gggcaaagtc       240
caagtcacgc ccctgatcca tgacgcgtc atgtatctgg caaacccggg cgacgtgatc       300
caggccatcg acgccaaaac tggcgatctg atctgggaac accgccgcca actgccgaac      360
atcgccacgc tgaacagctt tggcgagccg acccgcggca tggcgctgta cggcaccaac      420
gtttactttg tttcgtggga caaccacctg gtcgccctcg acaccgcaac tggccaagtg      480
acgttcgacg tcgaccgcgg ccaaggcgaa gacatggttt cgaactcgtc gggcccgatc      540
gtggcaaacg gcgtgatcgt tgccggttcg acctgccaat actcgccgtt cggctgcttt      600
gtctcgggcc acgactcggc caccggtgaa gagctgtggc gcaactactt catcccgcgc      660
gctggcgaag agggtgatga gacttggggc aacgattacg aagcccgttg gatgaccggt      720 gcctgggcc agatcaccta tgaccccgtc accaaccttg tccactacgg ctcgaccgct      780
gtgggtccgg cgtcggaaac ccaacgcggc accccgggcg gcacgctgta cggcacgaac      840
acccgtttcg ccgtgcgtcc tgacacgggc gagattgtct ggcgtcacca gaccctgccc      900
cgcgacaact gggaccagga atgcacgttc gagatgatgg tcaccaatgt ggatgtccaa      960
ccctcgaccg agatggaagg tctgcagtcg atcaacccga acgccgcaac tggcgagcgt     1020
cgcgtgctga ccggcgttcc gtgcaaaacc ggcaccatgt ggcagttcga cgccgaaacc     1080
ggcgaattcc tgtgggcccg tgataccaac taccagaaca tgatcgaatc catcgacgaa     1140
aacggcatcg tgaccgtgaa cgaagatgcg atcctgaagg aactggatgt tgaatatgac     1200
gtctgcccga ccttcttggg cggccgcgac tggccgtcgg ccgcactgaa ccccgacagc     1260
ggcatctact tcatcccgct gaacaacgtc tgctatgaca tgatggccgt cgatcaggaa     1320
```

```
ttcacctcga tggacgtcta taacaccagc aacgtgacca agctgccgcc cggcaaggat    1380
atgatcggtc gtattgacgc gatcgacatc agcacgggtc gtacgctgtg gtcggtcgaa    1440
cgtgctgcgg cgaactattc gcccgtcttg tcgaccggcg gcggcgttct gttcaacggt    1500
ggtacggatc gttacttccg cgccctcagc caagaaaccg gcgagaccct gtggcagacc    1560
cgccttgcaa ccgtcgcgtc gggccaggcc atctcttacg aggttgacgg catgcaatat    1620
gtcgccatcg caggtggtgg tgtcagctat ggctcgggcc tgaactcggc actggctggc    1680
gagcgagtcg actcgaccgc catcggtaac gccgtctacg tcttcgccct gccgcaataa    1740

<210> SEQ ID NO 2
<211> LENGTH: 1740
<212> TYPE: DNA
<213> ORGANISM: Gluconobacter oxydans

<400> SEQUENCE: 2
atgaagacgt cgtctttgct ggttgcgagc gttgccgcgc ttgcaagcta tagctccttt      60
gcgcttgctc aagtgacccc cgtcaccgat gaattgctgg cgaacccgcc cgctggtgaa     120
tggatcagct acggtcagaa ccaagaaaac taccgtcact cgcccctgac gcagatcacg     180
actgagaacg tcgccaact gcaactggtc tgggcgcgcg gcatgcagcc gggcaaagtc     240
caagtcacgc ccctgatcca tgacggcgtc atgtatctgg caaacccggg cgacgtgatc     300
caggccatca cgccaaaac tggcgatctg atctgggaac accgccgcca actgccgaac     360
atcgccacgc tgaacagctt tggcgagccg acccgcggca tggcgctgta cggcaccaac     420
gtttactttg tttcgtggga caaccacctg gtcgccctcg acaccgcaac tggccaagtg     480
acgttcgacg tcgaccgcgg ccaaggcgaa gacatggttt cgaactcgtc gggcccgatc     540
gtggcaaacg cgtgatcgt tgccggttcg acctgccaat actcgccgtt cggctgcttt     600
gtctcgggcc acgactcggc caccggtgaa gagctgtggc gcaactactt catcccgcgc     660
gctggcgaag agggtgatga gacttggggc aacgattacg aagcccgttg gatgaccggc     720
gtctggggtc agatcaccta tgaccccgtt ggcggccttg tccactacgg ctcgtcggct     780
gttggcccgg cttcggaaac ccagcgcggc accaccggcg gcaccatgta cggcaccaac     840
acccgtttcg ctgtccgtcc cgagactggc gagatcgtct ggcgtcacca aactctgccc     900
cgcgacaact gggaccaaga gtgcaccttc gagatgatgg ttgccaacgt tgacgtgcag     960
cccgcagctg acatggacgg cgtccgctcg atcaacccga acgccgccac cggcgagcgt    1020
cgcgttctga ccggcgttcc gtgcaaaacc ggcaccatgt ggcagttcga cgccgaaacc    1080
ggcgaattcc tgtgggcccg tgacaccagc tacgagaaca tcatcgaatc gatcgacgaa    1140
aacggcatcg tgaccgtcga cgagtcgaaa gttctgaccg agctggacac cccctatgac    1200
gtctgcccgc tgctgctggg tggccgtgac tggccgtcgg ctgcgctgaa ccccgatacc    1260
ggcatctact ttatcccgct gaacaacacc tgcatggata tcgaagctgt cgaccaggaa    1320
ttcagctcgc tggacgtgta caaccaaagc ctgaccgcca aaatggcacc gggtaaagag    1380
ctggttggcc gtatcgacgc catcgacatc agcacaggcc gcaccctgtg gaccgctgag    1440
cgcgaagcct cgaactacgc gcctgtcctg tcgaccgctg gcggcgttct gttcaacggc    1500
ggcaccgacc gttacttccg cgctctcagc caagagaccg gcgagaccct gtggcagacc    1560
cgtctggcga ctgtcgcttc gggccaagct gtctcgtacg agatcgacgg cgtccaatac    1620
atcgccatcg gcggcggcgg cacgacctat ggttcgttcc acaaccgtcc cctggccgag    1680
```

-continued

| ccgtcgact cgaccgcgat cggtaatgcg atgtacgtct tcgcgctgcc ccagcaataa | 1740 |

<210> SEQ ID NO 3
<211> LENGTH: 1737
<212> TYPE: DNA
<213> ORGANISM: Gluconobacter oxydans

<400> SEQUENCE: 3

| atgaaactga cgaccctgct gcaaagcagc gccgccctgc ttgtgcttgg caccattccc | 60 |
| gcccttgccc aaaccgccat caccgatgaa atgctggcga accgccccgc tggtgaatgg | 120 |
| atcaactacg gtcagaacca agagaactac cgccactcgc ccctgacgca gattaccgca | 180 |
| gacaacgtcg gccaactgca actggtctgg gcgcgcggta tggaagcggg caagatccaa | 240 |
| gtgaccccgc ttgtccatga cggcgtcatg tatctggcaa ccccggtga cgtgatccag | 300 |
| gccatcgacg ccgcgaccgg cgatctgatc tgggaacacc gccgccaact gccgaacatc | 360 |
| gccacgctga acagctttgg tgagccgacc cgcggcatgg ccctctatgg caccaacgtc | 420 |
| tatttcgtct cgtgggacaa ccacttggtc gcgctggaca cctcgaccgg ccaagtcgta | 480 |
| ttcgacgtcg atcgcggtca aggcacggat atggtctcga actcgtccgg cccgattgtc | 540 |
| gccaatggcg tcatcgttgc gggctcgacc tgtcagtatt cgccgttcgg ctgtttcgtt | 600 |
| tcgggccacg actcggccac cggtgaagag ctgtggcgca cacctttat cccgcgcgcc | 660 |
| ggcgaagagg gtgatgagac ctggggcaat gattacgagg cccgctggat gaccggcgtt | 720 |
| tggggccaga tcacctatga ccccgttggc ggccttgtcc actacggcac ctcagcagtt | 780 |
| ggccctgcgg ccgagattca gcgcggcacc gttggcggct cgatgtatgg caccaacacc | 840 |
| cgctttgctg tccgccccga gaccggcgag atcgtctggg tcaccaaaac tctgccccgc | 900 |
| gacaactggg accaagagtg tacgttcgag atgatggtcg tcaacgtcga cgtccagccc | 960 |
| tcggctgaga tggaaggcct gcacgccatc aaccccgatg ccgccacggg cgagcgtcgc | 1020 |
| gttgtgaccg gcgttccgtg caagaacggc accatgtggc agttcgacgc cgaaaccggc | 1080 |
| gaattcctgt gggcgcgcga caccagctat cagaacctga tcgaaagcgt cgatcccgat | 1140 |
| ggtctggtgc atgtgaacga agatctggtc gtgaccgagc tggaagtggc ctatgaaatc | 1200 |
| tgcccgacct tcctggggtgg ccgcgactgg ccgtcggctg cgctgaaccc cgatactggc | 1260 |
| atctatttca tcccgctgaa caacgcctgt agcggtatga cggctgtcga ccaagagttc | 1320 |
| agctcgctcg atgtgtataa cgtcagcctc gactataaac tgtcgcccgg ttcggaaaac | 1380 |
| atgggccgta tcgacgccat cgacatcagc accggccgca cgctgtggtc ggctgaacgc | 1440 |
| tacgcctcga actacgcgcc tgtcctgtcc accggcggcg cgtgctgttt caacggcggc | 1500 |
| accgaccgtt acttccgcgc cctcagccaa gagaccggcg agacgctgtg cagacccgt | 1560 |
| ctggcgactg tcgcctcggg tcaagcgatt tcctatgaga tcgacggcgt gcaatatgtc | 1620 |
| gccatcgggc gcggcggcac cagctatggc agcaaccaca accgcgccct gaccgagcgg | 1680 |
| atcgactcga ccgccatcgg cagcgcgatc tatgtctttg ctctgccgca gcagtaa | 1737 |

<210> SEQ ID NO 4
<211> LENGTH: 1740
<212> TYPE: DNA
<213> ORGANISM: Gluconobacter oxydans

<400> SEQUENCE: 4

| atgaacccca caacgctgct tcgcaccagc gcggccgtgc tattgcttac cgcgcccgcc | 60 |
| gcattcgcgc aggtaacccc gattaccgat gaactgctgg cgaacccgcc cgctggtgaa | 120 |

-continued

```
tggattaact acggccgcaa ccaagaaaac tatcgccact cgcccctgac ccagatcact    180
gccgacaacg ttggtcagtt gcaactggtc tgggcccgcg ggatggaggc ggggccgta    240
caggtcacgc cgatgatcca tgatggcgtg atgtatctgg caaaccccgg tgatgtgatc    300
caggcgctgg atgcgcaaac aggcgatctg atctgggaac accgccgcca actgcccgcc    360
gtcgccacgc taaacgccca aggcgaccgc aagcgcggcg tcgcccttta cggcacgagc    420
ctctatttca gctcatggga caaccatctg atcgcgctgg atatggagac gggccaggtc    480
gtattcgatg tcgaacgtgg atcgggcgaa acggcttga ccagtaacac cacggggccg    540
attgtcgcca atggcgtcat cgtcgcgggt tccacctgcc aatattcgcc ctatggatgc    600
tttatctcgg ggcacgattc cgcgacgggt gaggagctgt ggcgcaacca ctttatcccg    660
cagccgggcg aagagggtga cgagacttgg ggcaatgatt tcgaggcgcg ctggatgacc    720
ggcgtctggg gtcagatcac ctatgatccc gtgacgaacc ttgtgttcta tggctcgacc    780
ggcgtgggcc cagcgtccga acccagcgc ggcacgccgg cggcacgct gtatggcacc    840
aacacccgct tgcggtgcg tcccgacacg ggcgagattg tctggcgtca ccagaccctg    900
ccgcgcgaca actgggacca agaatgcacg ttcgagatga tggtcgccaa cgtcgatgtg    960
caaccctcgg ccgagatgga gggtctgcgc gccatcaacc ccaatgcggc gacgggcgag   1020
cgccgtgtgc tgacgggtgc gccttgcaag accggcacga tgtggtcgtt tgatgcggcc   1080
tcgggcgaat tcctgtgggc gcgtgatacc aactacacca atatgatcgc ctcgatcgac   1140
gagaccggcc ttgtgacggt gaacgaggat gcggtgctga agagctgga cgttgaatat   1200
gacgtctgcc cgaccttcct gggtgggcgc gactggtcgt cagccgcact gaacccggac   1260
accggcattt acttcttgcc gctgaacaat gcctgctacg atattatggc cgttgatcaa   1320
gagtttagcg cgctcgacgt ctataacacc agcgcgaccg caaaactcgc gccgggcttt   1380
gaaaatatgg gccgcatcga cgcgattgat atcagcaccg ggcgcacctt gtggtcggcg   1440
gagcgccctg cggcgaacta ctcgcccgtt ttgtcgacgg caggcggtgt ggtgttcaac   1500
ggcgggaccg accgctattt ccgtgccctc agccaggaaa ccggcgagac tttgtggcag   1560
gcccgtcttg cgacggtcgc gacggggcag gcgatcagct acgagttgga cggcgtgcaa   1620
tatatcgcca tcggtgcggg cggtctgacc tatggcacgc aattgaacgc gccgctggcc   1680
gaggcaatcg attcgacctc ggtcggtaat gcgatctatg tctttgcact gccgcagtaa   1740
```

<210> SEQ ID NO 5
<211> LENGTH: 579
<212> TYPE: PRT
<213> ORGANISM: Gluconobacter oxydans
<220> FEATURE:
<221> NAME/KEY: SIGNAL
<222> LOCATION: (1)..(23)
<223> OTHER INFORMATION:

<400> SEQUENCE: 5

Met Lys Pro Thr Ser Leu Leu Trp Ala Ser Ala Gly Ala Leu Ala Leu
1               5                   10                  15

Leu Ala Ala Pro Ala Phe Ala Gln Val Thr Pro Val Thr Asp Glu Leu
            20                  25                  30

Leu Ala Asn Pro Pro Ala Gly Glu Trp Ile Ser Tyr Gly Gln Asn Gln
        35                  40                  45

Glu Asn Tyr Arg His Ser Pro Leu Thr Gln Ile Thr Thr Glu Asn Val
    50                  55                  60

-continued

```
Gly Gln Leu Gln Leu Val Trp Ala Arg Gly Met Gln Pro Gly Lys Val
 65                  70                  75                  80

Gln Val Thr Pro Leu Ile His Asp Gly Val Met Tyr Leu Ala Asn Pro
                 85                  90                  95

Gly Asp Val Ile Gln Ala Ile Asp Ala Lys Thr Gly Asp Leu Ile Trp
                100                 105                 110

Glu His Arg Arg Gln Leu Pro Asn Ile Ala Thr Leu Asn Ser Phe Gly
            115                 120                 125

Glu Pro Thr Arg Gly Met Ala Leu Tyr Gly Thr Asn Val Tyr Phe Val
        130                 135                 140

Ser Trp Asp Asn His Leu Val Ala Leu Asp Thr Ala Thr Gly Gln Val
145                 150                 155                 160

Thr Phe Asp Val Asp Arg Gly Gln Gly Glu Asp Met Val Ser Asn Ser
                165                 170                 175

Ser Gly Pro Ile Val Ala Asn Gly Val Ile Val Ala Gly Ser Thr Cys
                180                 185                 190

Gln Tyr Ser Pro Phe Gly Cys Phe Val Ser Gly His Asp Ser Ala Thr
            195                 200                 205

Gly Glu Glu Leu Trp Arg Asn Tyr Phe Ile Pro Arg Ala Gly Glu Glu
        210                 215                 220

Gly Asp Glu Thr Trp Gly Asn Asp Tyr Glu Ala Arg Trp Met Thr Gly
225                 230                 235                 240

Ala Trp Gly Gln Ile Thr Tyr Asp Pro Val Thr Asn Leu Val His Tyr
                245                 250                 255

Gly Ser Thr Ala Val Gly Pro Ala Ser Glu Thr Gln Arg Gly Thr Pro
                260                 265                 270

Gly Gly Thr Leu Tyr Gly Thr Asn Thr Arg Phe Ala Val Arg Pro Asp
            275                 280                 285

Thr Gly Glu Ile Val Trp Arg His Gln Thr Leu Pro Arg Asp Asn Trp
        290                 295                 300

Asp Gln Glu Cys Thr Phe Glu Met Met Val Thr Asn Val Asp Val Gln
305                 310                 315                 320

Pro Ser Thr Glu Met Glu Gly Leu Gln Ser Ile Asn Pro Asn Ala Ala
                325                 330                 335

Thr Gly Glu Arg Arg Val Leu Thr Gly Val Pro Cys Lys Thr Gly Thr
            340                 345                 350

Met Trp Gln Phe Asp Ala Glu Thr Gly Glu Phe Leu Trp Ala Arg Asp
        355                 360                 365

Thr Asn Tyr Gln Asn Met Ile Glu Ser Ile Asp Glu Asn Gly Ile Val
    370                 375                 380

Thr Val Asn Glu Asp Ala Ile Leu Lys Glu Leu Asp Val Glu Tyr Asp
385                 390                 395                 400

Val Cys Pro Thr Phe Leu Gly Gly Arg Asp Trp Pro Ser Ala Ala Leu
                405                 410                 415

Asn Pro Asp Ser Gly Ile Tyr Phe Ile Pro Leu Asn Asn Val Cys Tyr
                420                 425                 430

Asp Met Met Ala Val Asp Gln Glu Phe Thr Ser Met Asp Val Tyr Asn
            435                 440                 445

Thr Ser Asn Val Thr Lys Leu Pro Pro Gly Lys Asp Met Ile Gly Arg
        450                 455                 460

Ile Asp Ala Ile Asp Ile Ser Thr Gly Arg Thr Leu Trp Ser Val Glu
465                 470                 475                 480

Arg Ala Ala Ala Asn Tyr Ser Pro Val Leu Ser Thr Gly Gly Gly Val
```

-continued

```
                        485                 490                 495
Leu Phe Asn Gly Gly Thr Asp Arg Tyr Phe Arg Ala Leu Ser Gln Glu
                500                 505                 510
Thr Gly Glu Thr Leu Trp Gln Thr Arg Leu Ala Thr Val Ala Ser Gly
            515                 520                 525
Gln Ala Ile Ser Tyr Glu Val Asp Gly Met Gln Tyr Val Ala Ile Ala
        530                 535                 540
Gly Gly Gly Val Ser Tyr Gly Ser Gly Leu Asn Ser Ala Leu Ala Gly
545                 550                 555                 560
Glu Arg Val Asp Ser Thr Ala Ile Gly Asn Ala Val Tyr Val Phe Ala
                565                 570                 575
Leu Pro Gln

<210> SEQ ID NO 6
<211> LENGTH: 579
<212> TYPE: PRT
<213> ORGANISM: Gluconobacter oxydans
<220> FEATURE:
<221> NAME/KEY: SIGNAL
<222> LOCATION: (1)..(23)
<223> OTHER INFORMATION:

<400> SEQUENCE: 6

Met Lys Thr Ser Ser Leu Leu Val Ala Ser Val Ala Ala Leu Ala Ser
1               5                   10                  15
Tyr Ser Ser Phe Ala Leu Ala Gln Val Thr Pro Val Thr Asp Glu Leu
                20                  25                  30
Leu Ala Asn Pro Pro Ala Gly Glu Trp Ile Ser Tyr Gly Gln Asn Gln
            35                  40                  45
Glu Asn Tyr Arg His Ser Pro Leu Thr Gln Ile Thr Thr Glu Asn Val
        50                  55                  60
Gly Gln Leu Gln Leu Val Trp Ala Arg Gly Met Gln Pro Gly Lys Val
65                  70                  75                  80
Gln Val Thr Pro Leu Ile His Asp Gly Val Met Tyr Leu Ala Asn Pro
                85                  90                  95
Gly Asp Val Ile Gln Ala Ile Asp Ala Lys Thr Gly Asp Leu Ile Trp
            100                 105                 110
Glu His Arg Arg Gln Leu Pro Asn Ile Ala Thr Leu Asn Ser Phe Gly
        115                 120                 125
Glu Pro Thr Arg Gly Met Ala Leu Tyr Gly Thr Asn Val Tyr Phe Val
    130                 135                 140
Ser Trp Asp Asn His Leu Val Ala Leu Asp Thr Ala Thr Gly Gln Val
145                 150                 155                 160
Thr Phe Asp Val Asp Arg Gly Gln Gly Glu Asp Met Val Ser Asn Ser
                165                 170                 175
Ser Gly Pro Ile Val Ala Asn Gly Val Ile Ala Gly Ser Thr Cys
            180                 185                 190
Gln Tyr Ser Pro Phe Gly Cys Phe Val Ser Gly His Asp Ser Ala Thr
        195                 200                 205
Gly Glu Glu Leu Trp Arg Asn Tyr Phe Ile Pro Arg Ala Gly Glu Glu
    210                 215                 220
Gly Asp Glu Thr Trp Gly Asn Asp Tyr Glu Ala Arg Trp Met Thr Gly
225                 230                 235                 240
Val Trp Gly Gln Ile Thr Tyr Asp Pro Val Gly Gly Leu Val His Tyr
                245                 250                 255
```

```
Gly Ser Ser Ala Val Gly Pro Ala Ser Glu Thr Gln Arg Gly Thr Thr
                260                 265                 270

Gly Gly Thr Met Tyr Gly Thr Asn Thr Arg Phe Ala Val Arg Pro Glu
            275                 280                 285

Thr Gly Glu Ile Val Trp Arg His Gln Thr Leu Pro Arg Asp Asn Trp
        290                 295                 300

Asp Gln Glu Cys Thr Phe Glu Met Met Val Ala Asn Val Asp Val Gln
305                 310                 315                 320

Pro Ala Ala Asp Met Asp Gly Val Arg Ser Ile Asn Pro Asn Ala Ala
                325                 330                 335

Thr Gly Glu Arg Arg Val Leu Thr Gly Val Pro Cys Lys Thr Gly Thr
            340                 345                 350

Met Trp Gln Phe Asp Ala Glu Thr Gly Glu Phe Leu Trp Ala Arg Asp
                355                 360                 365

Thr Ser Tyr Glu Asn Ile Ile Glu Ser Ile Asp Glu Asn Gly Ile Val
        370                 375                 380

Thr Val Asp Glu Ser Lys Val Leu Thr Glu Leu Asp Thr Pro Tyr Asp
385                 390                 395                 400

Val Cys Pro Leu Leu Leu Gly Gly Arg Asp Trp Pro Ser Ala Ala Leu
                405                 410                 415

Asn Pro Asp Thr Gly Ile Tyr Phe Ile Pro Leu Asn Asn Thr Cys Met
            420                 425                 430

Asp Ile Glu Ala Val Asp Gln Glu Phe Ser Ser Leu Asp Val Tyr Asn
                435                 440                 445

Gln Ser Leu Thr Ala Lys Met Ala Pro Gly Lys Glu Leu Val Gly Arg
        450                 455                 460

Ile Asp Ala Ile Asp Ile Ser Thr Gly Arg Thr Leu Trp Thr Ala Glu
465                 470                 475                 480

Arg Glu Ala Ser Asn Tyr Ala Pro Val Leu Ser Thr Ala Gly Gly Val
                485                 490                 495

Leu Phe Asn Gly Gly Thr Asp Arg Tyr Phe Arg Ala Leu Ser Gln Glu
            500                 505                 510

Thr Gly Glu Thr Leu Trp Gln Thr Arg Leu Ala Thr Val Ala Ser Gly
        515                 520                 525

Gln Ala Val Ser Tyr Glu Ile Asp Gly Val Gln Tyr Ile Ala Ile Gly
        530                 535                 540

Gly Gly Thr Thr Tyr Gly Ser Phe His Asn Arg Pro Leu Ala Glu
545                 550                 555                 560

Pro Val Asp Ser Thr Ala Ile Gly Asn Ala Met Tyr Val Phe Ala Leu
                565                 570                 575

Pro Gln Gln

<210> SEQ ID NO 7
<211> LENGTH: 578
<212> TYPE: PRT
<213> ORGANISM: Gluconobacter oxydans
<220> FEATURE:
<221> NAME/KEY: SIGNAL
<222> LOCATION: (1)..(23)
<223> OTHER INFORMATION:

<400> SEQUENCE: 7

Met Lys Leu Thr Thr Leu Leu Gln Ser Ala Ala Leu Leu Val Leu
1               5                   10                  15

Gly Thr Ile Pro Ala Leu Ala Gln Thr Ala Ile Thr Asp Glu Met Leu
            20                  25                  30
```

-continued

```
Ala Asn Pro Pro Ala Gly Glu Trp Ile Asn Tyr Gly Gln Asn Gln Glu
         35                  40                  45
Asn Tyr Arg His Ser Pro Leu Thr Gln Ile Thr Ala Asp Asn Val Gly
 50                  55                  60
Gln Leu Gln Leu Val Trp Ala Arg Gly Met Glu Ala Gly Lys Ile Gln
 65                  70                  75                  80
Val Thr Pro Leu Val His Asp Gly Val Met Tyr Leu Ala Asn Pro Gly
                 85                  90                  95
Asp Val Ile Gln Ala Ile Asp Ala Thr Gly Asp Leu Ile Trp Glu
             100                 105                 110
His Arg Arg Gln Leu Pro Asn Ile Ala Thr Leu Asn Ser Phe Gly Glu
             115                 120                 125
Pro Thr Arg Gly Met Ala Leu Tyr Gly Thr Asn Val Tyr Phe Val Ser
130                 135                 140
Trp Asp Asn His Leu Val Ala Leu Asp Thr Ser Thr Gly Gln Val Val
145                 150                 155                 160
Phe Asp Val Asp Arg Gly Gln Gly Thr Asp Met Val Ser Asn Ser Ser
                165                 170                 175
Gly Pro Ile Val Ala Asn Gly Val Ile Val Ala Gly Ser Thr Cys Gln
             180                 185                 190
Tyr Ser Pro Phe Gly Cys Phe Val Ser Gly His Asp Ser Ala Thr Gly
             195                 200                 205
Glu Glu Leu Trp Arg Asn Thr Phe Ile Pro Arg Ala Gly Glu Glu Gly
             210                 215                 220
Asp Glu Thr Trp Gly Asn Asp Tyr Glu Ala Arg Trp Met Thr Gly Val
225                 230                 235                 240
Trp Gly Gln Ile Thr Tyr Asp Pro Val Gly Gly Leu Val His Tyr Gly
                 245                 250                 255
Thr Ser Ala Val Gly Pro Ala Ala Glu Ile Gln Arg Gly Thr Val Gly
                 260                 265                 270
Gly Ser Met Tyr Gly Thr Asn Thr Arg Phe Ala Val Arg Pro Glu Thr
             275                 280                 285
Gly Glu Ile Val Trp Arg His Gln Thr Leu Pro Arg Asp Asn Trp Asp
290                 295                 300
Gln Glu Cys Thr Phe Glu Met Met Val Val Asn Val Asp Val Gln Pro
305                 310                 315                 320
Ser Ala Glu Met Glu Gly Leu His Ala Ile Asn Pro Asp Ala Ala Thr
                 325                 330                 335
Gly Glu Arg Arg Val Val Thr Gly Val Pro Cys Lys Asn Gly Thr Met
             340                 345                 350
Trp Gln Phe Asp Ala Glu Thr Gly Glu Phe Leu Trp Ala Arg Asp Thr
             355                 360                 365
Ser Tyr Gln Asn Leu Ile Glu Ser Val Asp Pro Asp Gly Leu Val His
         370                 375                 380
Val Asn Glu Asp Leu Val Val Thr Glu Leu Glu Val Ala Tyr Glu Ile
385                 390                 395                 400
Cys Pro Thr Phe Leu Gly Gly Arg Asp Trp Pro Ser Ala Ala Leu Asn
                 405                 410                 415
Pro Asp Thr Gly Ile Tyr Phe Ile Pro Leu Asn Asn Ala Cys Ser Gly
             420                 425                 430
Met Thr Ala Val Asp Gln Glu Phe Ser Ser Leu Asp Val Tyr Asn Val
             435                 440                 445
```

```
Ser Leu Asp Tyr Lys Leu Ser Pro Gly Ser Glu Asn Met Gly Arg Ile
    450                 455                 460

Asp Ala Ile Asp Ile Ser Thr Gly Arg Thr Leu Trp Ser Ala Glu Arg
465                 470                 475                 480

Tyr Ala Ser Asn Tyr Ala Pro Val Leu Ser Thr Gly Gly Val Leu
                485                 490                 495

Phe Asn Gly Gly Thr Asp Arg Tyr Phe Arg Ala Leu Ser Gln Glu Thr
            500                 505                 510

Gly Glu Thr Leu Trp Gln Thr Arg Leu Ala Thr Val Ala Ser Gly Gln
        515                 520                 525

Ala Ile Ser Tyr Glu Ile Asp Gly Val Gln Tyr Val Ala Ile Gly Arg
    530                 535                 540

Gly Gly Thr Ser Tyr Gly Ser Asn His Asn Arg Ala Leu Thr Glu Arg
545                 550                 555                 560

Ile Asp Ser Thr Ala Ile Gly Ser Ala Ile Tyr Val Phe Ala Leu Pro
                565                 570                 575

Gln Gln

<210> SEQ ID NO 8
<211> LENGTH: 579
<212> TYPE: PRT
<213> ORGANISM: Gluconobacter oxydans
<220> FEATURE:
<221> NAME/KEY: SIGNAL
<222> LOCATION: (1)..(23)
<223> OTHER INFORMATION:

<400> SEQUENCE: 8

Met Asn Pro Thr Thr Leu Leu Arg Thr Ser Ala Ala Val Leu Leu Leu
1               5                   10                  15

Thr Ala Pro Ala Ala Phe Ala Gln Val Thr Pro Ile Thr Asp Glu Leu
            20                  25                  30

Leu Ala Asn Pro Pro Ala Gly Glu Trp Ile Asn Tyr Gly Arg Asn Gln
        35                  40                  45

Glu Asn Tyr Arg His Ser Pro Leu Thr Gln Ile Thr Ala Asp Asn Val
    50                  55                  60

Gly Gln Leu Gln Leu Val Trp Ala Arg Gly Met Glu Ala Gly Ala Val
65                  70                  75                  80

Gln Val Thr Pro Met Ile His Asp Gly Val Met Tyr Leu Ala Asn Pro
                85                  90                  95

Gly Asp Val Ile Gln Ala Leu Asp Ala Gln Thr Gly Asp Leu Ile Trp
                100                 105                 110

Glu His Arg Arg Gln Leu Pro Ala Val Ala Thr Leu Asn Ala Gln Gly
            115                 120                 125

Asp Arg Lys Arg Gly Val Ala Leu Tyr Gly Thr Ser Leu Tyr Phe Ser
130                 135                 140

Ser Trp Asp Asn His Leu Ile Ala Leu Asp Met Glu Thr Gly Gln Val
145                 150                 155                 160

Val Phe Asp Val Glu Arg Gly Ser Gly Glu Asp Gly Leu Thr Ser Asn
                165                 170                 175

Thr Thr Gly Pro Ile Val Ala Asn Gly Val Ile Val Ala Gly Ser Thr
            180                 185                 190

Cys Gln Tyr Ser Pro Tyr Gly Cys Phe Ile Ser Gly His Asp Ser Ala
        195                 200                 205

Thr Gly Glu Glu Leu Trp Arg Asn His Phe Ile Pro Gln Pro Gly Glu
    210                 215                 220
```

Glu Gly Asp Glu Thr Trp Gly Asn Asp Phe Glu Ala Arg Trp Met Thr
225                 230                 235                 240

Gly Val Trp Gly Gln Ile Thr Tyr Asp Pro Val Thr Asn Leu Val Phe
            245                 250                 255

Tyr Gly Ser Thr Gly Val Gly Pro Ala Ser Glu Thr Gln Arg Gly Thr
            260                 265                 270

Pro Gly Gly Thr Leu Tyr Gly Thr Asn Thr Arg Phe Ala Val Arg Pro
            275                 280                 285

Asp Thr Gly Glu Ile Val Trp Arg His Gln Thr Leu Pro Arg Asp Asn
290                 295                 300

Trp Asp Gln Glu Cys Thr Phe Glu Met Met Val Ala Asn Val Asp Val
305                 310                 315                 320

Gln Pro Ser Ala Glu Met Gly Leu Arg Ala Ile Asn Pro Asn Ala
            325                 330                 335

Ala Thr Gly Glu Arg Arg Val Leu Thr Gly Ala Pro Cys Lys Thr Gly
            340                 345                 350

Thr Met Trp Ser Phe Asp Ala Ala Ser Gly Glu Phe Leu Trp Ala Arg
            355                 360                 365

Asp Thr Asn Tyr Thr Asn Met Ile Ala Ser Ile Asp Glu Thr Gly Leu
370                 375                 380

Val Thr Val Asn Glu Asp Ala Val Leu Lys Glu Leu Asp Val Glu Tyr
385                 390                 395                 400

Asp Val Cys Pro Thr Phe Leu Gly Gly Arg Asp Trp Ser Ser Ala Ala
            405                 410                 415

Leu Asn Pro Asp Thr Gly Ile Tyr Phe Leu Pro Leu Asn Asn Ala Cys
            420                 425                 430

Tyr Asp Ile Met Ala Val Asp Gln Glu Phe Ser Ala Leu Asp Val Tyr
            435                 440                 445

Asn Thr Ser Ala Thr Ala Lys Leu Ala Pro Gly Phe Glu Asn Met Gly
            450                 455                 460

Arg Ile Asp Ala Ile Asp Ile Ser Thr Gly Arg Thr Leu Trp Ser Ala
465                 470                 475                 480

Glu Arg Pro Ala Ala Asn Tyr Ser Pro Val Leu Ser Thr Ala Gly Gly
            485                 490                 495

Val Val Phe Asn Gly Gly Thr Asp Arg Tyr Phe Arg Ala Leu Ser Gln
            500                 505                 510

Glu Thr Gly Glu Thr Leu Trp Gln Ala Arg Leu Ala Thr Val Ala Thr
            515                 520                 525

Gly Gln Ala Ile Ser Tyr Glu Leu Asp Gly Val Gln Tyr Ile Ala Ile
            530                 535                 540

Gly Ala Gly Gly Leu Thr Tyr Gly Thr Gln Leu Asn Ala Pro Leu Ala
545                 550                 555                 560

Glu Ala Ile Asp Ser Thr Ser Val Gly Asn Ala Ile Tyr Val Phe Ala
            565                 570                 575

Leu Pro Gln

<210> SEQ ID NO 9
<211> LENGTH: 82
<212> TYPE: DNA
<213> ORGANISM: synthetic oligonucleotide

<400> SEQUENCE: 9
catgaaaata aaaacaggtg cacgcatcct cgcattatcc gcattaacga cgatgatgtt     60

-continued

```
ttccgcctcg gctctcgccc ag                                              82

<210> SEQ ID NO 10
<211> LENGTH: 83
<212> TYPE: DNA
<213> ORGANISM: synthetic oligonucleotide

<400> SEQUENCE: 10
gttacctggg cgagagccga ggcggaaaac atcatcgtcg ttaatgcgga taatgcgagg      60
atgcgtgcac ctgttttat ttt                                              83

<210> SEQ ID NO 11
<211> LENGTH: 27
<212> TYPE: PRT
<213> ORGANISM: Escherichia coli
<220> FEATURE:
<221> NAME/KEY: SIGNAL
<222> LOCATION: (1)..(26)
<223> OTHER INFORMATION:

<400> SEQUENCE: 11

Met Lys Ile Lys Thr Gly Ala Arg Ile Leu Ala Leu Ser Ala Leu Thr
1               5                   10                  15

Thr Met Met Phe Ser Ala Ser Ala Leu Ala Gln
            20                  25

<210> SEQ ID NO 12
<211> LENGTH: 27
<212> TYPE: DNA
<213> ORGANISM: synthetic oligonucleotide

<400> SEQUENCE: 12
gttagcgcgg tggatcccca ttggagg                                         27
```

ALCOHOL/ALDEHYDE DEHYDROGENASE

This is a continuation of U.S. application Ser. No. 08/934,506, filed Sep. 19, 1997 now abandonded.

FIELD OF THE INVENTION

The present invention relates to recombinant enzymes, particularly, novel recombinant alcohol/aldehyde dehydrogenases (hereinafter referred to as AADH or AADHs) having alcohol and aldehyde dehydrogenase activity. The present invention also relates to novel recombinant DNA molecules encoding AADHs, recombinant expression vectors containing said DNAs, and recombinant organisms containing said recombinant DNA molecules and/or said recombinant expression vectors. Furthermore, the present invention relates to a process for producing recombinant AADHs and a process for producing aldehydes, carboxylic acids and ketones, especially, 2-keto-L-gulonic acid (herein after referred to as 2KGA) by utilizing said recombinant enzymes, and a process for producing aldehydes, carboxylic acids and ketones, especially, 2KGA by utilizing said recombinant organisms.

BACKGROUND OF THE INVENTION

2-KGA is an important intermediate for the production of L-ascorbic acid (vitamin C). For example, 2KGA can be converted into ascorbic acid according to the well-known Reichstein method Numerous microorganisms are known to produce 2KGA from D-sorbitol or L-sorbose. Japanese Patent Publication No. 51-40154 (1976) discloses the production of 2KGA from D-sorbitol by microorganisms of the genus Acetobacter, Bacterium or Pseudomonas. According to Acta Microbiologica Sinica 21(2), 185–191 (1981), 2KGA can be produced from L-sorbose by a mixed culture of microorganisms, especially, *Pseudomonas striata* and *Gluconobacter oxydans*. European Patent Publication No. 0221 707 discloses the production of 2KGA from L-sorbose by *Pseudogluconobacter saccharoketogenes* with and without concomitant bacteria. European Patent Publication No. 0278 447 discloses a process for the production of 2KGA from L-sorbose by a mixed culture, which is composed of strain DSM No. 4025 (*Gluconobacter oxydans*) and DSM No. 4026 (a *Bacillus megaterium* strain). European Patent Publication No. 88116156 discloses a process for the production of 2KGA from L-sorbose by *Gluconobacter oxydans* DSM No. 4025.

From *G. oxydans* DSM No. 4025, AADH was purified and characterized to catalyze the oxidation of alcohols and aldehydes, and was thus capable of producing the corresponding aldehydes and ketones from alcohols, and carboxylic acids from aldehydes (see European Patent Publication No. 606621). More particularly, the AADH catalyzed the oxidation of L-sorbose to 2KGA via L-sorbosone. The physico-chemical properties of the purified sample of the AADH were as follows:

a) Optimum pH: about 7.0–9.0
b) Optimum temperature: about 20° C.–40° C.
c) Molecular weight: 135,000+/−5,000 dalton (Consisting of two subunits in any combination of such α-subunit and β-subunit, each having a molecular weight of 64,500+/−2,000 and 62,500+/−2,000, respectively)
d) Substrate specificity: active on primary and secondary alcohols and aldehydes including L-sorbose, L-sorbosone, D-sorbitol, D-glucose, D-mannitol, D-fructose, DL-glyceraldehyde, ethanol, 1-propanol, 1-butanol, 1-pentanol, 1-hexanol, 1-heptanol, 2-propanol, 2-butanol, propionaldehyde, PEG1000, PEG2000, PEG4000, PEG6000 and polyvinyl alcohol
e) Prosthetic group: pyrroloquinoline quinone
f) Isoelectric point: about 4.4

Once the genes coding for said AADH have been cloned, they can be used for the construction of a recombinant organism capable of producing a large amount of the recombinant AADH or the various aldehydes, ketones and carboxylic acids, especially, 2KGA. However, there have been no reports so far of the cloning of such genes.

SUMMARY OF THE INVENTION

The present invention relates to novel recombinant AADHs having alcohol and aldehyde dehydrogenase activity. Comprised by the present invention are novel recombinant molecules encoding the AADHs; recombinant expression vectors containing said DNAs; recombinant organisms carrying the DNAs and/or recombinant expression vectors; a process for producing the recombinant AADHs; and a process for producing aldehydes, carboxylic acids and ketones, especially, 2KGA utilizing the recombinant AADHs or the recombinant organisms.

More particularly, an aspect of the present invention concerns a recombinant enzyme having alcohol and aldehyde dehydrogenase activity which comprises one or more recombinant polypeptides which contain an amino acid sequence selected from SEQ ID NO 5, SEQ ID NO 6, SEQ ID NO 7, SEQ ID NO 8 and functional derivatives thereof which contain addition, insertion, deletion and/or substitution of one or more amino acid residues, wherein the recombinant polypeptides have said alcohol and aldehyde dehydrogenase activity.

The present invention also provides AADH enzymes which comprise chimeric recombinant polypeptides that are a chimeric combination of at least two of the following amino acid sequences identified by SEQ ID NO 5, SEQ ID NO 6, SEQ ID NO 7, SEQ ID NO 8, and functional derivatives thereof which contain addition, insertion, deletion and/or substitution of one or more amino acid residues, wherein the recombinant polypeptides have said alcohol and aldehyde dehydrogenase activity.

Another aspect of the present invention concerns a recombinant DNA molecule encoding at least one recombinant polypeptide containing an amino acid sequence selected from SEQ ID NO 5, SEQ ID NO 6, SEQ ID NO 7, SEQ ID NO 8, chimeric combinations of at least two of the following amino acid sequences identified by SEQ ID NO 5, SEQ ID NO 6, SEQ ID NO 7, SEQ ID NO 8, and functional derivatives thereof which contain addition, insertion, deletion and/or substitution of one or more amino acid residues, wherein said recombinant polypeptides have said alcohol and aldehyde dehydrogenase activity.

The recombinant DNA molecules of the present invention contain DNA sequences encoding the polypeptides with alcohol and aldehyde dehydrogenase activity as disclosed, e.g., in the sequence listings herein as well as their complementary strands, or those which include these sequences, DNA sequences which hybridize under standard conditions with such sequences or fragments thereof, and DNA sequences which because of the degeneracy of the genetic code, do not hybridize under standard conditions with such sequences but which code for polypeptides having exactly the same amino acid sequence.

Further aspects of the present invention concern a recombinant expression vector which carries one or more of the recombinant DNA molecules defined above and a recombinant organism which carries the recombinant expression vector defined above and/or carries one or more recombinant DNA molecules on a chromosome.

A further aspect of the present invention concerns a process for producing a recombinant enzyme having an alcohol and aldehyde dehydrogenase activity as defined above, which comprises cultivating a recombinant organism defined above in an appropriate culture medium and recovering said recombinant enzyme.

Another aspect of the present invention concerns a process for producing an aldehyde, ketone or carboxylic acid product from a corresponding substrate which comprises converting said substrate into the product by the use of a recombinant organism as defined above.

Moreover another aspect of the present invention concerns a process for producing 2-keto-L-gulonic acid which comprises the fermentation of a recombinant organism as defined above in an appropriate medium containing L-sorbose and/or D-sorbitol.

Another aspect of the present invention concerns a process for producing an aldehyde, ketone or carboxylic acid product from a corresponding substrate which comprises the incubation of a reaction mixture containing a recombinant enzyme of the present invention.

Furthermore another aspect of the present invention concerns a process for producing 2-keto-L-gulonic acid which comprises the incubation of a reaction mixture containing a recombinant AADH and L-sorbose and/or D-sorbitol.

It is also an object of the present invention to provide an intermediate, i.e., 2-keto-L-gulonic acid, for the production of vitamin C whereby a process for the production of 2-keto-L-gulonic acid as described above is effected and the 2-keto-L-gulonic acid obtained by such process is transformed into vitamin C (L-ascorbic acid) by methods known in the art.

Before describing the present invention in more detail a short explanation of the attached figures is given.

BRIEF DESCRIPTION OF THE DRAWINGS

FIG. 3 schematically illustrates the structures of the material plasmids each carrying a recombinant DNA molecule containing tandem structural genes of Enzyme A and Enzyme B for constructing the chimeras by a homologous recombination method.

FIG. 5 shows the alignment of the amino acid sequences of the mature Enzyme A and Enzyme B.

DETAILED DESCRIPTION OF THE INVENTION

Figure 1:
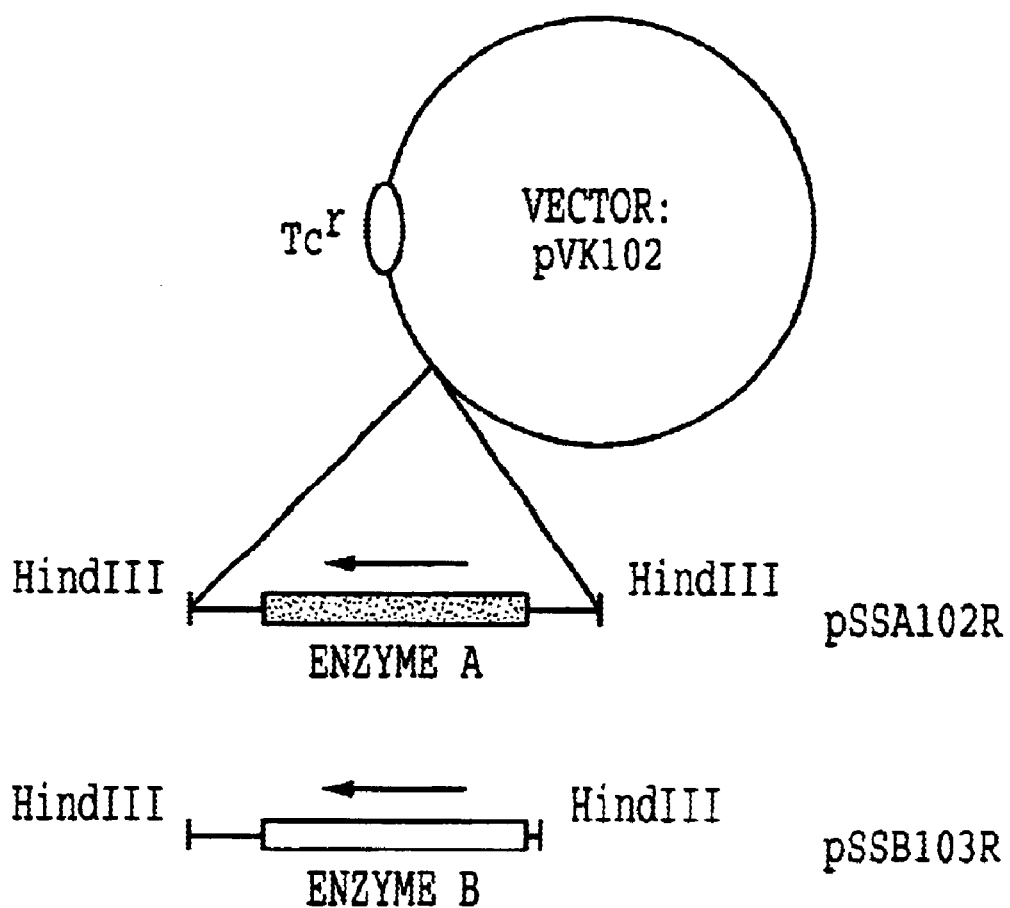
FIG. 1 schematically illustrates the structures of the recombinant expression vectors each carrying a recombinant DNA molecule which encodes a recombinant Enzyme A or B of the present invention.

The AADH genes of the present invention encode AADH enzymes capable of catalyzing the oxidation of various alcohols and aldehydes as described above. Specifically, particular genes encoding AADHs present in Gluconobacter were cloned and expressed. Alternative organisms from which AADH genes can be obtained, may be identified by one skilled in the art using the teachings of the present invention.

A specific and preferred *Gluconobacter oxydans* strain has been deposited at the Deutsche Sammlung von Mikroorganismen in Göttingen (Germany) under DSM No. 4025.

Moreover, a subculture of the strain has also been deposited in the Agency of Industrial Science and Technology, Fermentation Research Institute, Japan, under the deposit No.: FERM BP-3812. European Patent publication No. 0278 477 discloses the characteristics of this strain.

The AADH genes and the recombinant microorganisms utilized in the present invention can be obtained by the following steps:
(1) Cloning the AADH genes from a chromosomal DNA by colony- or plaque-hybridization, PCR cloning, Western-blot analysis, Southern-blot hybridization and the like;
(2) Determining the nucleotide sequences of such AADH genes by usual methods and constructing recombinant expression vectors which contain and express AADH genes efficiently; and
(3) Constructing recombinant microorganisms carrying recombinant AADH genes on recombinant expression vectors or on chromosomes by transformation, transduction, transconjugation and electroporation.

The materials and the techniques applicable to the above aspect of the present invention are exemplified in details as described in the following:

A total chromosomal DNA can be purified by a procedure well known in the art (Marmur J., J. Mol. Biol. 3:208, 1961). Then, a genomic library of the strain for such genes can be constructed with the chromosomal DNA and the vectors described below in detail. The genes encoding AADHs can be cloned in either plasmid or phage vectors from the total chromosomal DNA by the following methods:

(i) determining the partial amino acid sequences of the purified enzyme, according to the sequence information, synthesizing the oligonucleotides, and selecting the objective gene from the gene library by Southern-blot-, colony-, or plaque-hybridization;

(ii) by amplifying the partial sequence of the desired gene by polymerase chain reaction (PCR) with the oligonucleotides synthesized as described above as the primers and with the PCR product as a probe, selecting the complete sequence of the objective gene from the gene library by Southern-blot-, colony-, or plaque-hybridization;

(iii) by preparing the antibody reacting against the desired enzyme protein by such a method as previously described, e.g. in Methods in Enzymology, vol. 73, p 46, 1981, and selecting the clone which expresses the desired polypeptide by immnunological analysis including Western-blot analysis; and (iv) by aligning the amino acid sequences of the homologs to the one of the desired enzyme, selecting the amino acid sequences which are well conserved, synthesizing the oligonucleotides encoding the conserved sequences, amplifying the partial sequence of the desired gene by PCR with the above oligonucleotides as the primers, and selecting the complete sequence as described above (ii).

The nucleotide sequence of the desired gene can be determined by a well known method such as the dideoxy chain termination method with the M13 phage (Sanger F., et al., Proc. Natl. Acad. Sci. USA, 74:5463–5467, 1977).

By using the information of the so determined nucleotide sequence (in consideration of the codon usage) a gene encoding evolutionally divergent alcohol/aldehyde dehydrogenases, can be isolated from a different organism by colony- or Southern-hybridization with a probe synthesized according to the amino acid sequence deduced from said nucleotide sequence or by the polymerase chain reaction with primers also synthesized according to said information, if necessary.

To express the desired gene or generally speaking the desired DNA sequence of the present invention efficiently, various promoters can be used; for example, the original promoter of said gene, promoters of antibiotic resistance genes such as the kanamycin resistant gene of Tn5 (Berg, D. E., and C. M. Berg. 1983. Bio/Technology 1:417–435), the ampicillin resistant gene of pBR322, a promoter of the beta-galactosidase gene of *Escherichia coli* (lac), trp-, tac-trc-promoter, promoters of lambda phages and any promoters which can be functional in the hosts consisting of microorganisms including bacteria such as *E. coli, P. putida, Acetobacter xylinum, A. pasteurianus, A. aceti, A. hansenii* and *G. oxydans*, mammalian and plant cells.

Furthermore other regulatory elements, such as a Shine-Dalgarno (SD) sequence (for example, AGGAGG etc. including natural and synthetic sequences operable in the host cell) and a transcriptional terminator (inverted repeat structure including any natural and synthetic sequence operable in the host cell) which are operable in the host cell into which the coding sequence will be introduced can be used with the above described promoters.

DNA encoding a signal peptide containing from about 15 to about 50 amino acid residues can be used to obtain expression of periplasmic AADH polypeptides. DNA encoding a signal peptide can be selected from any natural or synthetic sequence operable in the host cell.

A wide variety of host/cloning vector combinations may be employed in cloning the double-stranded DNA. Suitable cloning vectors are generally plasmids or phage which contain a replication origin, regulatory elemtents, a cloning site including a multi-cloning site and selection markers such as antibiotic resistance genes including resistance genes for ampicillin, tetracycline, kanamycin, streptomycin, gentamicin, spectinomycin, etc.

Preferred vectors for the expression of the DNA sequences of the present invention in *E. coli* are selected from any vectors usually used in *E. coli*, such as pBR322 or its derivatives including pUC18 and pBluescript II, pACYC177 and pACYC184(J. Bacteriol., 134:1141–1156, 1978) and their derivatives, and a vector derived from a broad host range plasmid such as RK2 and RSF1010. A preferred vector for the expression of the DNA sequences of the present invention in Gluconobacter including *G. oxydans* DSM No. 4025 and *P. putida* is selected from any vectors which can replicate in Gluconobacter and/or *P. putida*, as well as a preferred cloning organism such as *E. coli*. The preferred vector is a broad-host-range vector such as a cosmid vector like pVK102 and its derivatives and RSF1010 and its derivatives, and a vector containing a replication origin functional in Gluconobacter and another origin functional in *E. coli*. Copy number and stability of the vector should be carefully considered for stable and efficient expression of the cloned gene and also for efficient cultivation of the host cell carrying the cloned gene. DNA molecules containing transposable elements such as Tn5 can be also used as a vector to introduce the DNA sequence of the present invention into the preferred host, especially on a chromosome. DNA molecules containing any DNAs isolated from the preferred host together with the desired DNA sequence of the present invention are also useful to introduce the desired DNA sequence of the present invention into the preferred host, especially on a chromosome. Such DNA molecules can be transferred to the preferred host by transformation, transduction, transconjugation or electroporation.

Useful hosts may include microorganisms, mammalian cells, plant cells and the like. Preferable microorganisms, are bacteria such as *E. coli, P. putida, A. xylinum, A. pasteurianus, A. aceti, A. hansenii, G. oxydans*, and any Gram-negative bacteria which are capable of producing recombinant AADHs. In accordance with the present invention, functional equivalents, subcultures, mutants and variants of said microorganism can also be used. Preferred strains are *E. coli* K12 and its derivatives, *P. putida* or *G. oxydans* DSM No. 4025.

The functional AADH encoding DNA sequence of the present invention is ligated into a suitable vector containing a regulatory region such as a promoter and a ribosomal binding site operable in the host cell described above using well-known methods in the art to produce an expression plasmid. Structures of such recombinant expression vectors are specifically shown in FIGS. 1, 2, 4, and 10.

To construct a recombinant microorganism carrying a recombinant expression vector, various gene transfer methods including transformation, transduction, conjugal mating (Chapters 14 and 15, Methods for general and molecular bacteriology, Philipp Gerhardt et al. ed., American Society for Microbiology, (1994), and electroporation can be used. The method for constructing a recombinant organism may be selected from the methods well-known in the field of molecular biology. Usual transformation systems can be used for *E. coli*, Pseudomonas and Acetobacter. A transduction system can also be used for *E. coli*. Conjugal mating systems can be widely used in Gram-positive and Gram-negative bacteria including *E. coli, P. putida* and *G. oxydans*.

A preferred conjugal mating method is described in WO89/06688. The conjugation can occur in liquid media or on a solid surface. The preferred recipient is selected from *E. coli, P. putida* and *G. oxydans* which can produce active AADHs with a suitable recombinant expression vector. The preferred recipient for 2KGA production is *G. oxydans* DSM No. 4025. To the recipient for conjugal mating, a selective marker is usually added; for example, resistance against nalidixic acid or rifampicin is usually selected.

The AADHs provided by the present invention catalyze the oxidation of alcohols and aldehydes, and are thus capable of producing aldehydes, ketones or carboxylic acids from corresponding substrates. More particularly, the AADHs provided by the present invention can catalyze the oxidation of L-sorbose to 2KGA via L-sorbosone and/or the oxidation of D-sorbitol to L-sorbose.

The present invention provides AADHs that include one or more of the following enzymes: Enzyme A, Enzyme A', Enzyme A", and Enzyme B, which contain the amino acid sequences shown in SEQ ID NO 5, SEQ ID NO 6, SEQ ID NO 7, and SEQ ID NO 8, respectively, and functional derivatives thereof that have alcohol and aldehyde dehydrogenase activity, i.e., for example can oxidize substrates to aldehydes, carboxylic acids and/or ketones. Furthermore, the AADHs herein include chimeric recombinant polypeptides having any number of and/or combination of amino acid sequences identified by SEQ ID NOS. 5, 6, 7, 8 and functional derivatives thereof that have alcohol and aldehyde dehydrogenase activity, i.e., for example can oxidize substrates to aldehydes, carboxylic acids and/or ketones.

Figure 6:
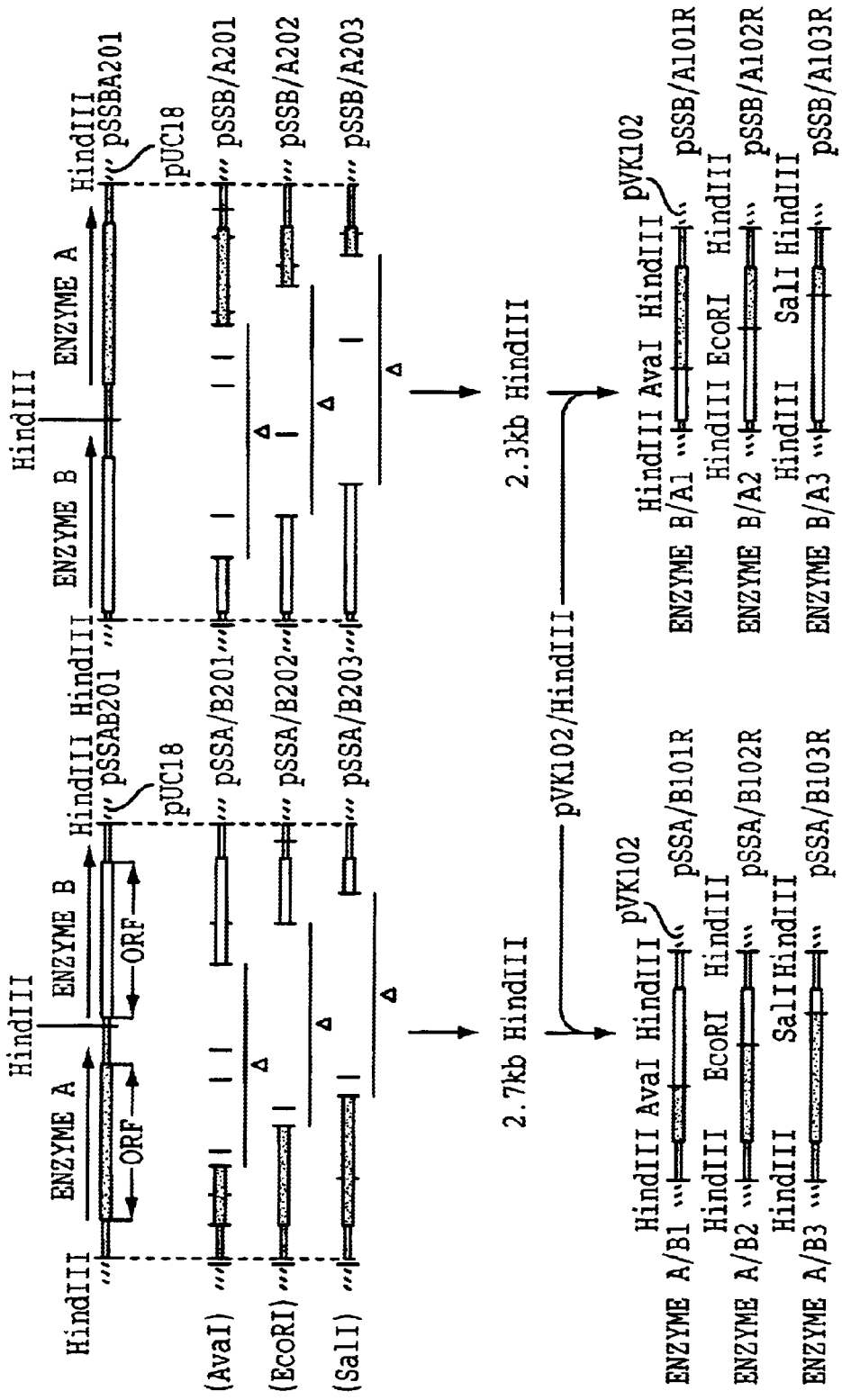
FIG. 6 illustrates the construction schemes of the recombinant genes encoding chimeric enzymes of the present invention.
Figure 8:
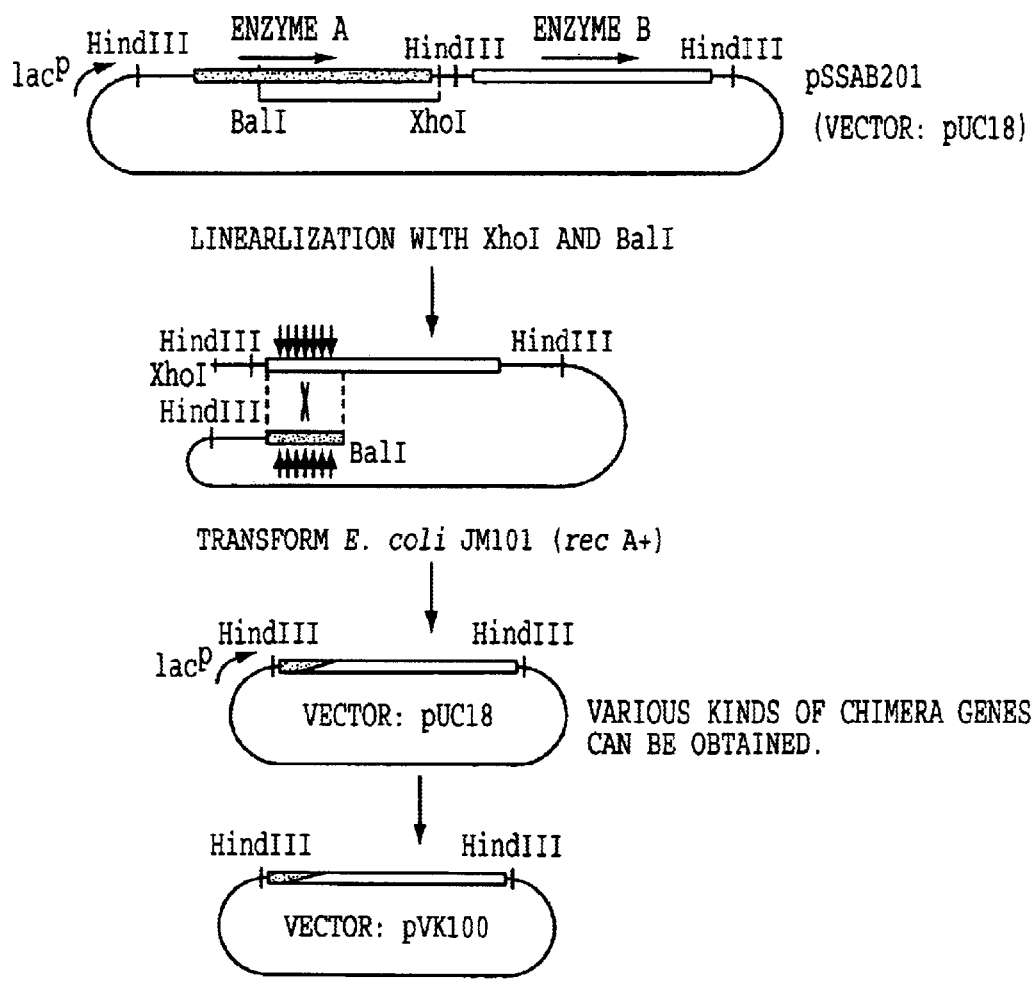
FIG. 8 illustrates the construction of chimeric genes by homologous recombination of two AADH genes in vivo at the conserved nucleotide sequences in both genes.

Chimeric recombinant polypeptides encoding the AADHs of the present invention can be produced by any conventional methods known in the art. For example, the chimeras can be prepared by combining two or more parts of DNA sequences of the present invention in vitro at the conserved restriction site in both sequences with restriction enzymes and T4-ligase as shown in FIG. 6, or by recombining two AADH genes in vivo at the conserved nucleotide sequences in both genes as shown in FIG. 8.

Functional derivatives of SEQ ID NOS. 5, 6, 7 and 8 contain addition, insertion, deletion and/or substitution of one or more amino acid residues of those sequences. Such functional derivatives can be made by conventional methods known in the art such as chemical peptide synthesis or by recombinant means, for example, those methods disclosed by Sambrook et al. (Molecular Cloning, Cold Spring Harbour Laboratory Press, New York, USA, second edition 1989). Amino acid exchanges in proteins and peptides which do not generally alter the activity of such molecules are known in the state of the art and are described, for example, by H. Neurath and R. L. Hill in "The Proteins" (Academic Press, New York, 1979, see especially Figure 6, page 14). The most commonly occurring exchanges are: Ala/Ser, Val/Ile, Asp/Glu, Thr/Ser, Ala/Gly, Ala/Thr, Ser/Asn, Ala/Val, Ser/Gly, Tyr/Phe, Ala/Pro, Lys/Arg, Asp/Asn, Leu/Ile, Leu/Val, Ala/Glu, Asp/Gly as well as these exchanges in reverse.

The functional derivatives of the AADH polypeptides also include polypeptides with additional polypeptides at the N-terminal, C-terminal and/or inside region of the AADH polypeptides. Enzyme B, Enzyme A/B25, and Enzyme A/B3 fused with cytochrome c polypeptides (17–18 kDa) of *G. oxydans* DSM 4025 at the C-terminus showed comparable AADH activities with their corresponding enzymes lacking the cytochrome c polypeptides i.e., Enzyme B described in Example 4 in the conversion of D-sorbitol to L-sorbose, and Enzyme A/B25 and Enzyme A/B3 both described in Example 14 in the conversion of L-sorbose to 2KGA. Thus, a relatively long polypeptide can be added or inserted to the AADHs provided by the present invention to form enzymes having comparable AADH activity.

The functional derivatives of the AADH polypeptides described above can have preferred characteristics such as a desired substrate specificity, higher affinity to a substrate, lower affinity to an inhibitory compound, higher stability against temperature and/or pH, and higher catalytic speed. As described in the working examples below, such derivatives would improve the productivity of the desired products. The alcohol and aldehyde dehydrogenase activity of enzymes that include recombinant polypeptides which contain amino acid sequences that are functional derivatives of SEQ ID NOS. 5, 6, 7, and/or 8 can be determined by conventional methods known in the art, such as the preferred standard assay described herein.

The enzymatic recombinant polypeptides of the present invention are usually produced in the form of dimers. Such dimers include homodimers of Enzyme A, A', A" or B, or the derivatives including chimeras, and heterodimers consisting of two different recombinant polypeptides mentioned above. Thus the recombinant enzymes of the present invention also contain one or more of said-homodimers and/or heterodimers.

The recombinant DNA molecules encoding the AADH polypeptides of the present invention contain DNA sequences selected from SEQ ID NO 1, SEQ ID NO 2, SEQ ID NO 3 and SEQ ID NO 4, as well as their complementary strands, or those which include these sequences, DNA sequences which hybridize under standard conditions with such sequences or fragments thereof and DNA sequences, which because of the degeneracy of the genetic code, do not hybridize under standard conditions with such sequences but which code for polypeptides having exactly the same amino acid sequence.

"Standard conditions" for hybridization mean in this context the conditions which are generally used by one skilled in the art to detect specific hybridization signals and which are described, e.g. by Sambrook et al., "Molecular Cloning" second edition, Cold Spring Harbor Laboratory Press 1989, New York. Such "standard conditions" are preferably stringent hybridization and non-stringent washing conditions, or more preferably, stringent hybridization and stringent washing conditions familiar to those skilled in the art and which are described, e.g. in Sambrook et al. (s.a.).

The DNA sequences encoding the AADHs of the present invention can be made by conventional methods known in the art, such as, for example, the polymerase chain reaction by using primers designed on the basis of the DNA sequences disclosed herein. It is understood that the DNA sequences of the present invention can also be made synthetically as described, e.g. in EP 747 483.

In accordance with the present invention, the DNA molecules encoding the AADH polypeptides described herein can be gene-homologs resulting from degeneracy of the genetic code or any sequence of natural, synthetic or recombinant origin which has significant homology to the AADH genes. The DNA sequence derivatives can be functional mutants of the polypeptides identified by SEQ ID NO 5, SEQ ID NO 6, SEQ ID NO 7 and SEQ ID NO 8 which contain addition, insertion, deletion and/or substitution of one or more amino acid residues, wherein the enzymatic polypeptides have alcohol and aldehyde dehydrogenase activity. The mutant genes can be prepared by any conventional method, such as, for example, treating AADH genes with a mutagen such as ultraviolet irradiation, X-ray irradiation, γ-ray irradiation or contact with a nitrous acid, N-methyl-N'-nitro-N-nitrosoguanidine (NTG), or other suitable mutagens, or isolating a clone occurring by spontaneous mutation or by standard methods of in vitro mutagenesis known in the art.

Enzyme A, A', A", and B genes, which have the nucleotide sequences shown in SEQ ID NOS. 1, 2, 3, and 4, respectively, and encode the polypeptides having the amino acid sequences shown in SEQ ID NOS. 5, 6, 7, and 8, respectively can be derived from G. oxydans strain DSM No. 4025.

The AADHs including Enzymes A, A', A" and B provided by the present invention can be produced from a recombinant organism by any conventional means for expressing, recovering and purifying a recombinant protein. For example, the enzyme can be obtained by culturing the recombinant organism containing the DNA encoding the enzyme so as to produce the enzyme, disrupting the recombinant organism, and isolating and purifying them from cell free extracts of the disrupted recombinant organism, preferably from the soluble fraction of the recombinant organism.

The recombinant organisms provided in the present invention may be cultured in an aqueous medium supplemented with appropriate nutrients under aerobic conditions. The cultivation may be conducted at a pH between about 4.0 and 9.0, preferably between about 6.0 and 8.0. While the cultivation period varies depending upon pH, temperature and nutrient medium used, usually 2 to 5 days will bring about favorable results. A preferred temperature range for carrying out the cultivation is from about 13° C. to 45° C. preferably from about 18° C. to 42° C.

It is usually required that the culture medium contains such nutrients as assimilable carbon sources, digestible nitrogen sources and inorganic substances, vitamins, trace elements and other growth promoting factors. As assimilable carbon sources, glycerol, D-glucose, D-mannitol, D-fructose, D-arabitol, D-sorbitol, L-sorbose, and the like can be used.

Various organic or inorganic substances may also be used as nitrogen sources, such as yeast extract, meat extract, peptone, casein, corn steep liquor, urea, amino acids, nitrates, ammonium salts and the like. As inorganic substances, magnesium sulfate, potassium phosphate, ferrous and ferric chlorides, calcium carbonate and the like may be used.

In the following, the properties of the purified recombinant AADH enzymes specifically from P. putida and the production method are summarized.

(1) Enzyme Activity

The AADHs of the present invention catalyze oxidation of alcohols and aldehydes including D-sorbitol, L-sorbose, and L-sorbosone in the presence of an electron acceptor according to the following reaction formula.

Alcohol+Electron acceptor→Aldehyde+Reduced electron acceptor

Alcohol+Electron acceptor→Ketone+Reduced electron acceptor

Aldehyde+Electron acceptor→Carboxylic acid+Reduced acceptor

Sugar alcohol+Electron acceptor→Aldose+Reduced electron acceptor

Sugar alcohol+Electron acceptor→Ketose+Reduced electron acceptor

Aldehyde ketose+Electron acceptor→Ketocarboxylic acid+Reduced electron acceptor

Carboxylic acid+Electron acceptor→Ketocarboxylic acid+Reduced electron acceptor

The enzymes herein do not utilize molecular oxygen as an acceptor. As an acceptor, 2,6-dichlorophenolindophenol (DCIP), phenazine methosulphate (PMS), Wurster's blue, ferricyanide, coenzyme Q or cytochrome c can be used.

The enzymatic activity of the AADHs herein can be determined by methods known in the art, such as by photometric analysis using a spectrophotometer. In accordance with the present invention, one unit of enzyme activity was defined as the amount of enzyme which catalyzed the reduction of 1 μmole of DCIP per minute. The extinction coefficient of DCIP at pH 8.0 was taken as 15 mM$^{-1}$. In a preferred standard assay for determining the enzyme activity of the AADHs herein, a first cuvette includes a standard reaction mixture (1.0 ml) containing 0.1 mM DCIP, 1 mM PMS, 2 to 125 mM substrate, 50 mM Tris-malate-NaOH buffer (pH 8.0), and 10 μl of the enzyme solution. A second cuvette, i.e., a reference cuvette, contains all the above components except the substrate. The reference cuvette is used to standardize the background absorbance resulting from a substrate-independent (endogenous) reaction. Preferably, a double beam spectrophotometer is used to determine the activity of the enzyme in the presence of a substrate with respect to a standard reaction mixture in the absence of the substrate.

(2) Properties of the AADHs a) Substrate Specificity and Products of the Enzymatic Reaction The Enzymes A, A', A" and B were characterized by their substrate specificities as described above using 8 substrates: n-propanol, isopropanol, D-glucose, D-sorbitol, L-sorbosone, D-mannitol, L-sorbose, and D-fructose. The results are indicated in Table 1.

TABLE 1

Substrate specificity of the Enzymes A, A', A"and B

| Substrate | Enzyme A | Enzyme A'* | Enzyme A" | Enzyme B |
|---|---|---|---|---|
| (units/mg of purified protein) | | | | |
| 50 mM n-Propanol | 139.6 | 180.7 | 262.3 | 40.0 |
| 50 mM Isopropanol | 76.8 | 108.9 | 154.9 | 72.3 |
| 50 mM D-Glucose | 2.4 | 0.0 | 17.8 | 943.9 |
| 125 mM D-Sorbitol | 14.0 | 7.8 | 30.1 | 130.9 |
| 2 mM L-Sorbosone | 23.15 | 5.0 | 26.5 | 73.6 |
| 50 mM D-Mannitol | 7.1 | 1.3 | 6.2 | 517.4 |
| 125 mM L-Sorbose | 47.4 | 1.6 | 30.3 | 8.4 |
| 125 mM D-Fructose | 30.7 | 2.9 | 17.3 | 2.1 |

*Values of the Enzyme A' was corrected by 1.5-fold, since purity of the enzyme was about 65%.

Enzyme B showed a high reactivity for D-glucose or D-mannitol, but relatively low reactivity for n-propanol and isopropanol. Enzyme A, Enzyme A' and Enzyme A" showed a high reactivity for n-propanol and isopropanol, but a low reactivity for D-glucose and D-mannitol; the enzymes showed similar substrate specificity patterns, except that the Enzyme A' had a very low reactivity for L-sorbose or D-fructose.

Products formed from a substrate in the reaction with Enzyme A, Enzyme A', Enzyme A" or Enzyme B were analyzed by thin layer chromatography (TLC) and/or high performance liquid chromatography (HPLC) with authentic compounds. Enzyme A, Enzyme A' and Enzyme A"

(designated A group) converted D-sorbitol, L-sorbose, L-sorbosone, D-mannitol, and D-fructose to D-glucose with L-gulose, L-sorbosone with 2KGA, 2KGA, D-mannose, and 2-keto-D-gluconic acid (2KD), respectively. Enzyme B (designated B group) converted D-glucose, D-sorbitol, L-sorbosone, D-mannitol, L-idose, glycerol, D-gluconic acid, D-mannoic acid to D-gluconate, L-sorbose, 2KGA, D-fructose, L-idonic acid, dihydroxyacetone, 5-keto-D-gluconic acid, and 5-keto-D-mannoic acid, respectively. Similarly to the reactivity for L-sorbosone, D-glucosone can be converted to 2KD by all of above mentioned AADHs. A group enzymes can produce 2KD from D-fructose whose possible direct product is D-glucosone. All of the enzymes showed the activity for alcohols including sugar alcohol such as D-sorbitol and D-mannitol, and aldehydes including aldose such as D-glucose and ketose such as L-sorbosone.

b) Optimum pH

All the enzymes have their optimal point at pH 8.0–8.5 as shown in Table 2. The Enzymes A" and B have a relatively wide pH range toward a lower pH, compared with the Enzymes A and A'.

TABLE 2

Optimal pH of the enzymes

| | (Relative activity, %) | | | |
|---|---|---|---|---|
| pH | Enzyme A | Enzyme A' | Enzyme A" | Enzyme B |
| 6.0 | 6.5 | 2.1 | 35.0 | 21.0 |
| 6.5 | 13.0 | 9.3 | 57.3 | 51.6 |
| 7.0 | 33.1 | 22.5 | 74.8 | 61.6 |
| 7.5 | 57.7 | 46.8 | 90.0 | 75.3 |
| 8.0 | 100.0 | 100.0 | 100.0 | 100.0 |
| 8.5 | 113.2 | 142.7 | 85.6 | 62.2 |
| 9.0 | 50.0 | 2.1 | 46.5 | 8.0 |
| 9.5 | 19.6 | 1.8 | 23.9 | 0.0 | c) pH Stability

Enzymes A, A', A" and B were incubated in buffers of various pH-values for 3 hours at 25° C. and the residual activities were assayed and expressed as relative values against that obtained by no incubation at pH 8. Enzymes A, A', A" and B were stable between pH 6 to 9 as shown in Table 3.

TABLE 3 pH stability of the enzymes

| | (Relative activity, %) | | | |
|---|---|---|---|---|
| pH | Enzyme A | Enzyme A' | Enzyme A" | Enzyme B |
| 4.0 | 5.4 | 0.0 | 6.2 | 25.2 |
| 5.0 | 32.0 | 10.0 | 77.9 | 56.1 |
| 6.0 | 74.7 | 82.7 | 105.8 | 100.9 |
| 7.0 | 76.9 | 96.9 | 100.9 | 101.9 |
| 8.0 | 80.1 | 100.0 | 99.0 | 114.0 |
| 9.0 | 60.1 | 97.3 | 100.9 | 101.9 |
| 10.0 | 53.2 | 85.4 | 104.0 | 85.5 |
| 11.0 | 31.0 | 61.3 | 79.2 | 70.1 | d) Thermal Stability

The residual activities after the treatment of the enzymes at 4, 20, 30, 40, 50, and 60° C. for 5 minutes are shown in Table 4.

TABLE 4

Thermal stability of the enzymes

| | (Relative activity, %) | | | |
|---|---|---|---|---|
| Temperature | Enzyme A | Enzyme A' | Enzyme A" | Enzyme B |
| 4° C. | 100.0 | 100.0 | 100.0 | 100.0 |
| 20° C. | 91.5 | 100.8 | 96.0 | 97.2 |
| 30° C. | 78.0 | 103.6 | 86.1 | 95.4 |
| 40° C. | 19.9 | 78.9 | 72.8 | 84.6 |
| 50° C. | 4.1 | 0.6 | 26.6 | 29.2 |
| 60° C. | 2.9 | 0.0 | 13.3 | 0.0 | e) Effect of Metal Ions and Inhibitors

Remaining activities after the treatment of the eyes with various metals and inhibitors are shown in Table 5. $MgCl_2$ and $CaCl_2$ were nearly inert to the enzymes, while the other metal ions, especially $CuCl_2$, significantly affected the reactivity. EGTA and EDTA inhibited the Enzymes A, A' and A", remarkably. However, Enzyme B was less inhibited than the A group enzymes by EDTA and EGTA.

TABLE 5

Effect of metals and inhibitors on activities of the Enzymes A, A', A" and B.

| | | (Relative remaining activity) | | | |
|---|---|---|---|---|---|
| Compound | Enzyme Substrate | A L-Sorbose | A' n-Propanol | A" L-Sorbose | B D-Sorbitol |
| 5 mM $CoCl_2$ | | 16.6 | 7.9 | 46.9 | 23.6 |
| 5 mM $CuCL_2$ | | 0.0 | 0.0 | 0.0 | 0.0 |
| 5 mM $ZnCl_2$ | | 1.5 | 6.1 | 19.2 | 0.0 |
| 5 mM $MgCl_2$ | | 96.3 | 85.3 | 78.8 | 100.0 |
| 5 mM $CaCl_2$ | | 98.8 | 95.3 | 123.0 | 102.9 |
| 5 mM $MmCl_2$ | | 0.0 | 45.7 | 0.0 | 0.0 |
| 5 mM $FeCl_2$ | | 16.6 | 0.0 | 0.0 | 5.9 |
| 5 mM $FeCl_3$ | | 7.8 | 0.0 | 44.7 | 0.0 |
| 5 mM $NiSO_4$ | | 42.7 | 59.7 | 90.3 | 79.4 |
| 10 mM EDTA | | 43.1 | 55.1 | 52.6 | 91.3 |
| 10 mM EGTA | | 20.4 | 16.7 | 56.4 | 74.0 |
| 1 mM NaF | | 98.2 | 97.1 | 94.9 | 100.8 |
| 2 mM NEM | | 91.7 | 97.2 | 94.9 | 100.8 |
| 1 mM $ICH_2COONa$ | | 97.2 | 78.3 | 95.3 | 100.2 |
| 0.5 mM Hydroxyl-amine-HCl | | 104.6 | 98.8 | 97.2 | 102.1 | f) Molecular Weight and Subunit

Enzymes A, A', A" and B purified from *P. putida* transconjugants consist of one type of unit with the molecular weight of about 64,000, 62,500, 62,500 and 60,000, respectively, as measured by sodium dodecyl sulfate polyacrylamide gel electrophoresis. They can be heterodimers consisting of any two units of Enzymes A, A', A" and B when DNA sequences encoding Enzymes A, A', A" and B are expressed in the same host.

g) N-terminal Amino Acid Sequence

N-terminal sequences of mature Enzymes A and B are

Enzyme A: Gln-Val-Thr-Pro-Val-Thr - - - -

Enzyme A" : Blocked N-terminal residue

Enzyme B: Gln-Val-Thr-Pro-Ile-Thr-Asp-Glu-Leu-Leu-Ala - - - . The N-terminus of the mature Enzyme A' is not determined because of an insufficient purity of the sample.

(3) Production of the AADHs

Cells are harvested from the fermentation broth by centrifugation or filtration. The cells are suspended in the buffer solution and disrupted by means of a homogenizer, sonicator or treatment with lysozyme and the like to give a disrupted solution of cells.

AADHs are isolated and purified from a cell free extract of disrupted cells, preferably from the soluble fraction of the microorganisms by usual protein purification methods such as ammonium sulfate precipitation, dialysis, ion exchange chromatographies, gel filtration chromatographies, and affinity chromatographies.

(4) Enzyme Reaction

Enzyme reaction was performed at pH values from about 6.0 to about 9.0 at the temperature of about 10° C. to about 50° C., and preferrably about 20° C. to 40° C. in the presence of an electron acceptor, for example, DCIP, PMS, Wurster's blue, ferricyanide, coenzyme Q, cytochrome c and the like in a buffer such as Tris-HCl buffer, phosphate buffer and the like. The concentration of the substrate in a reaction mixture can vary depending on the other reaction conditions but, in general, is desirable to be about 1–200 g/l, and most preferably from about 1–100 g/l.

In the enzyme reaction, AADHs may also be used in an immobilized state with an appropriate carrier. Any means of immobilizing enzymes generally known to the art may be used. For instance, the enzyme may be bound directly to membrane granules, or the like, of a resin having functional groups, or it may be bound through bridging compounds having functional groups, for example, glutaraldehyde, to the resin.

The recombinant organisms provided by the present invention are highly useful for the production of the recombinant enzymes having alcohol and aldehyde dehydrogenase activity. Said organisms are also useful for the production of aldehydes, carboxylic acids and ketones, especially, 2KGA by utilizing said recombinant enzymes, and by utilizing the recombinant organisms.

The production of 2KGA can be obtained from the recombinant organisms by fermentation of the recombinant organisms with the medium and culture conditions as described above. The production of 2KGA may be performed with the recombinant organisms described above together with concomitant organisms such as *E. coli, P. putida* and *Bacillus megaterium*.

In accordance with the present invention, 2KGA obtained by the methods described herein can be transformed into vitamin C (L-ascorbic acid) by methods known in the art.

EXAMPLES

Example 1

Cloning of AADH Genes (1) Construction of a Genomic Library of *G. oxydans* DSM No. 4025

Chromosomal DNA was prepared as follows. *G. oxydans* DSM No. 4025 was cultivated on an agar plate containing 20 ml of NS2 medium consisting of 5.0% D-mannitol, 0.25% $MgSO_4 \cdot 7H_2O$, 1.75% corn steep liquor, 5.0% baker's yeast (Oriental Yeast Co., Osaka, Japan), 0.5% $CaCO_3$, 0.5% urea (sterilized separately) and 2.0% agar (pH 7.0 before sterilization) at 27° C. for 3 days. The cells were collected from the agar plate, washed with 10 ml of 10 mM Tris-HCl buffer (pH 8.0) containing 1 mM EDTA and resuspended in 5 ml of 10 mM Tris-HCl buffer (pH 8.0) containing 20 mM EDTA. The cell suspension was treated with lysozyme (Sigma Chemicals Co., St. Louis, Mo., USA) at a final concentration of 400 µg/ml at 37° C. for 30 minutes, then with pronase (400 units) at 37° C. 30 minutes and with 1% SDS at 37° C. for 1 hour. Chromosomal DNA was treated with phenol and RNase A (Boheringer Mannheim, GmbH, Mannheim, Germany) according to the method described by Maniatis et al. (Molecular cloning: a laboratory manual. Cold Spring Harbor Laboratory, Cold Spring Harbor, N.Y., (1982). Chromosomal DNA (200 µg) was digested with 168 units of SalI (Boehringer Mannheimn) at 37° C. for 5 to 90 minutes. The resulting partially digested fragments of 15–35 kb were isolated by preparative agarose gel electrophoresis (agarose: 0.7%); the gel piece containing the desired fragments was cut out and the DNAs were electro-eluted from the gel into TAE buffer consisting of 40 mM Tris-acetate and 2 mM EDTA. Thus, 40 µg of the DNAs were obtained. In parallel, 8 µg of the cosmid vector pVK102 (ATCC 37158) was completely digested with SalI and treated with calf intestine alkaline phosphatase (Boehringer Mannheim) according to the supplier's recommendation. pVK102 (0.4 µg) was ligated with the 15–35 kb SalI fragments (0.2–2 µg) by the ligation kit (Takara Shuzo Co. Ltd., Kyoto, Japan) at 26° C. for 10 minutes. The ligated DNAs were then used for in vitro packaging according to the method described by the supplier (Amersham): mixing the ligated DNAs with the phage coat protein parts. The resulting phage particles were used to infect *E. coli* ED8767 (Murray, N. E., W. J. Brammar and K. Murray. Mol. Gen. Genet., 150:53–61, 1977). About 3,000 $Km^r Tc^s$ colonies were obtained and all of the colonies tested (24 colonies) possessed the insert DNAs; its average size was 26.5 kb. Another cosmid library of *G. oxydans* DSM No. 4025 containing 55,000 clones was constructed by using chromosomal DNA of *G. oxydans* DSM No. 4025 partially digested with EcoRI and inserting them into theEcoRI site of pVK100 by almost the same method described above. All of the colonies tested (24 colonies) possessed insert DNAs (average size; 27 kb).

These two cosmid libraries in *E. coli* ED8767 were then transferred into *E. coli* S 17-1 ($Tra^+$, Bio/Technology, 1:784–791, 1983) by using the mixture of recombinant plasmid DNAs extracted from *E. coli* ED8767 libraries. About 4,000 $Km^r$ transformants of *E. coli* S17-1 were picked up, cultivated individually in microtiter plates containing 100 µl of LB consisting of 10 g/l of Bactotrypton (Difco), 5 g/l of yeast extract (Difco) and 5 g/l of NaCl supplemented with 50 µg/ml kanamycin at 37° C., and stocked with 15% glycerol at −80° C. as cosmid libraries in *E. coli* S17-1.

The *G. oxydans* DSM No. 4025-SalI and -EcoRI cosmid libraries were constructed in *E. coli* S17-1. From the library, 1,400 clones were individually transferred from E. coli S17-1 into P. putida ATCC 21812 by conjugal mating. 1,400 cultures stocked in microtiter plates at −80° C. were thawed and transferred to microtiter plates containing 100 µl of fresh LB medium in each well with a plate transfer cartridge (Nunc) and cultivated at 37° C. overnight. Nalidixic acid resistant (Nal$^r$) P. putida ATCC21812 was cultivated at 30° C. overnight in 100 ml of MB medium consisting of 2.5% mannitol, 0.5% yeast extract (Difco Laboratories, Detroit, Mich.) and 0.3% Bactotryptone (Difco). Fifty µl of the P. putida culture was individually added to the 1,400 wells containing cultures of the cosmid library. The 1,400 cell mixtures were spotted with plate transfer cartridges onto nitrocellulose filters placed on the surface of FB agar medium consisting of 5% fructose, 1% yeast extract (Difco), 1% polypeptone (Daigo Eiyo, Japan) and 1.8% agar and cultivated at 27° C. overnight. Nalidixic acid was used for the counter-selection of transconjugants against donor E. coli. The cells grown on the filters were individually streaked onto MB agar medium containing 50 µg/ml of nalidixic acid and 50 µl/ml of kanamycin hereinafter referred to as (MNK agar plate) and incubated for 4 days at 27° C. for the selection of transconjugants. The resulting colonies were purified by streaking on MNK agar plates as mentioned above. Thus, 1,400 transconjugants of P. putida [gene library of G. oxydans DSM No. 4025 in P. putida] were prepared.

(2) Immunological Screening of Clones of the AADH Gene of G. oxydans DSM No. 4025.

At first, 350 transconjugants (175 from SalI library and 175 from EcoRI library) maintained MNK agar plates were individually cultivated in test tubes containing 5 ml of MNK medium The cells were collected from 1.5 ml of each broth and treated for Western-blot analysis as follows. The cells were suspended in 50 µl of Laemmli buffer consisting of 62.5 mM Tris-HCl, pH 6.8, 10% glycerol, 5% mercaptoethanol and 2% SDS. The cell suspension was boiled for 3 minutes, and 10 µl of the cell lysate was applied on SDS-PAGE. The resulting protein bands were then electro-blotted to a nitrocellulose filter by an electroblotting apparatus (Marysol Industrial Co., Ltd.) operated at 40 V, 200 mA for 16 hours in 2.5 mM Tris-19.2 mM glycine buffer, pH 8.6, containing 20% methanol. The filter was, then, incubated for 1 hour in 3% gelatin in TBS buffer consisting of 20 mM Tris, pH 7.5, and 500 mM NaCl. After a brief rinse in TTBS buffer consisting of 20 mM Tris, pH 7.5, 500 mM NaCl and 0.05% Tween 20, the filter was incubated for 1 hour with a first-antibody which contained 1:500 diluted anti-AADH antibody in TTBS buffer containing 1% gelatin. The anti-AADH antibody had been prepared by mixing the AADH proteins purified from G. oxydans DSM No. 4025 with incomplete adjuvant, injecting the resulting mixture into a white rabbit twice with 2 weeks' interval, collecting whole blood 1 week after the second injection and preparing the serum fraction as the anti-AADH antibody. Then, the filter was washed twice (5 min each) in TTBS buffer and incubated for 1 hour in a second-antibody (goat anti-rabbit IgG-horseradish peroxidase conjugate) solution which contained 1:3,000 diluted second antibody in TTBS containing 1% gelatin. After washing in TTBS buffer twice and in TBS once, the filter was immersed in a color developing solution until blue bands became visible with Konica Immunostaining HRP Kit IS-50B (Konica, Tokyo, Japan) according to the supplier's recommendation. For an actual screening, five cell lysates were mixed and applied to one well for the first Western-blot screening. Out of 70 mixtures, 14 exhibited positive bands; nine samples had immuno-reactive proteins of approximate Mr 64,000, but two of these exhibited weak signals; one had an immuno-reactive protein of approximate Mr 60,000; and four samples had immuno-reactive proteins of Mr 55,000.

Seven mixture samples showing strong signals at Mr 64,000 were individually subjected to a second Western-blot screening to identify the clone in each mixture. One positive clone per one mixture samples was identified; plasmids of the seven clones were designated as p6E10, p16C8, p16F4, p17E8, p1E2, p24D4, and p26C3, respectively. By restriction enzyme analysis, it was found that four plasmids, p6E10, p16C8, p16F4, and p17E8, carried the same DNA region and the other three carried different regions from that of the former four plasmids.

(3) Screening of the AADH Genes from the Cosmid Libraries by Colony-blot and Southern-blot Hybridization To find the other AADH genes besides the genes obtained by the immunological screening as described above, the whole cosmid libraries of G. oxydans DSM No. 4025 in E. coli ED 8767 (SalI-library and EcoRI-libraries) were screened by colony- and Southern-blot hybridization with a 0.9 kb SalI fragment of p24D4. The 0.9 kb SalI fragment hybridized with a oligonucleotide probe, ATGATGGT (GATC)AC(GATC)AA(TC)GT synthesized according to an internal amino acid sequence of the natural AADH enzyme purified from G. oxydans DSM No. 4025, MetMetValThrAsnValAspValGlnMetSerthrGlu, which was obtained by digestion and sequenced by automatic gas-phase sequencer (Applied Biosystems 470A). The cells of the cosmid libraries were appropriately diluted and spread on LK agar plates, and the resulting colonies were blotted onto nylon filters and were analyzed by hybridization with the $^{32}$P-labeled 0.9 kb SalI fragment. About 1% of the colonies showed positive signals; 41 colonies were selected from the SalI library and 20 from EcoRI library, and they were subjected to restriction enzyme analysis, followed by Southern-blot analysis. Six different AADH gene-related DNA regions were isolated in this screening as follows: four already-isolated regions carried on p24D4, p1E2, p26C3 and, p17E8, and two new regions carried on two separate plasmids designated as pSS31 and pSS53. The other plasmnid pSS33 carried both of the two regions which were carried on p24D4 and pSS31.

(4) Immunological and Enzymatic Characterization of AADH Clones

Western-blot analysis of cell lysates of P. putida carrying p24D4, p1E2, p26C3, pSS31 and p17E8 showed that the five clones encoded proteins with molecular weights of about 64,000, 62,500, 62,500, 60,000 and 62,000, respectively. Plasmid pSS33 encoded two immuno-reactive proteins with molecular weights of about 64,000 and 60,000, whereas pSS53 did not produce any immuno-reactive proteins.

Enzyme activities of each clone (cell free extract, soluble fraction and membrane fraction) were measured by photometric analysis. The cells of each clone were inoculated in 5 ml of MB medium in a test tube and cultivated at 30° C. for 24 hours. The resulting broth was transferred into 200 ml of fresh MB medium in 500 ml flask and the flask was shaken on the rotary flask shaker at 30° C. for 24 hours. The cells were collected by centrifugation at 6,000×g for 10 minutes and washed with 40 ml of cold buffer consisting of 50 mM Tris-HCl, pH 7.5, 5 mM MgCl$_2$ and 0.5 mM phenylmethylsulfonyl fluoride and suspended with the same buffer to prepare cell suspension of 1 g wet cells per 5 ml. The cell suspension was subjected twice to a French press cell disruptor (1,500 kg/cm$^2$) and the resulting homogenate was centrifuged at 6,000×g for 10 minutes to remove cell debris. Thus obtained cell free extract (CFE) was centrifuged at 100,000×g for 60 minutes. The resulting supernatant and pellet were collected as the cytosol fraction and the membrane fraction, respectively and subjected to PMS-DCIP assay as follows. The enzyme reaction mixture (1.0 ml) contained 100 µM DCIP, 1 mM PMS, 50 mM Tris malate-NaOH buffer, pH 8.0, a substrate and the enzyme (10 µl). Substrate-dependent decreasing rate of absorbance of DCIP at 600 nm was measured at 25° C. by using a Kontron spectrophotometer UVIKON 810. Table 6 shows the level of enzyme activities in the cell free extract and the soluble fractions of the clones. According to the substrate specificity, the enzyme encoded on each plasmid was classified into large three groups, A-, B- and C-groups: A-group catalyzes the oxidation of L-sorbose, D-sorbitol and 1-propanol; B-group catalyzes the oxidation of D-glucose and D-sorbitol; C-group showed no clearly detectable activities on the substrates used. In the A-group, there were three types, A, A' and A" each of which was distinguished from each other by their physical map of the DNA carried on each plasmid. B- or C-group each consisted of only one type of protein derived from one region of the chromosomal DNA.

TABLE 7

Homologies of amino acid sequences among AADHs.

|  | Enzyme A | Enzyme A' | Enzyme A" | (%) Enzyme B |
|---|---|---|---|---|
| Enzyme A | 100 | — | — | — |
| Enzyme A' | 89 | 100 | — | — |
| Enzyme A" | 85 | 86 | 100 | — |
| Enzyme B | 83 | 82 | 81 | 100 |

FIG. 5 shows the amino acid sequences of mature Enzyme A and Enzyme B which are aligned so as to be comparable.

Homology search of Enzymes A, A', A" and B revealed that Enzymes A, A', A" and B showed rather low homology (26–31% homology through the polypeptides) with several quino-proteins including alcohol dehydrogenase of *Acetobacter aceti* (T. Inoue et al., J. Bacteriol. 171:3115–3122) or *Acetobacter polyoxogenes* (T. Tamaki et al., B. B. A., 1088:292–300), and methanol dehydrogenase of *Paracoccus denitrificans* (N. Harms et al., J. Bacteriol., 169:3966–3975), *Methylobacterium organophilum* (S. M.

TABLE 6

| Enzyme Group | Enzyme Name | Plasmid | CFE Sorbose 125 mM | Soluble fraction | | | | |
|---|---|---|---|---|---|---|---|---|
| | | | | Sorbose*1 125 mM | Glucose*2 50 mM | Sorbitol*3 125 mM | Sorbosone*4 2 mM | n-Propanol 50 mM |
| A | A | p24D4 | +++ | +++ | − | +++ | +++ | ++++ |
| A | A' | p1E2 | + | + | − | + | + | + |
| A | A" | p26C3 | + | + | − | +/− | + | + |
| B | B | pSS31 | − | − | ++++ | ++ | + | + |
| C | — | p17E8 | − | − | +/− | − | − | − |
| A and B | A and B | pSS33 | +++ | +++ | ++++ | ++++ | +++ | ++++ |

Level of the activity;
++++: very high
+++: high
++: medium
+: low
+/−: trace
−: not detected
*1–*4Oxidation product of each substrate was determined by a resting cell reaction followed by TLC analysis.
*1Oxidation product of L-sorbose by Enzymes A, A', A", and [A and B] was 2KGA.
*2Oxidation product of D-glucose by Enzyme B, and Enzeyms [A and B] was D-gluconic acid.
*3Oxidation product of D-sorbitol by Enzymes A, A', and A" was mainly D-glucose; that by Enzyme B was L-sorbose; and that by Enzymes [A and B] was mixture of D-glucose and L-sorbose.
*4Oxidation product of L-sorbosone by Enzymes A, A', A", B, and [A and B] was 2KGA.

Example 2

Nucleotide Sequencing

Nucleotide sequences of the genes for Enzymes A, A', A" and B were determined with the plasmids, p24D4, p1E2, p26C3, and pSS31, respectively, by the dideoxynucleotide chain termination method using M13mp18 and M13mp19 (Boehringer Mannheim). One open reading frame (ORF) for each gene was found; the nucleotide sequences of the four genes are shown in the sequence list SEQ ID NOS. 1 to 4 and the amino acid sequences deduced from the nucleotide sequences were shown in the sequence list SEQ ID NOS. 5 to 8. The ORFs for Enzymes A, A', A" and B genes are 1737, 1737, 1734, and 1737-bp long and encode 579, 579, 578 and 579 amino acid residues all including 23 amino acid of signal sequences.

The homologies between Enzymes A, A', A" and B are shown in Table 7.

Machlin et al., J. Bacteriol., 170:4739–4747), or *Methylobacterium extorquens* (D. J. Anderson et al., Gene 90:171–176).

Example 3

Subcloning of AADH Genes

Enzyme A gene was originally cloned as a cosmid clone of p24D4 which has about 25 kb insert in EcoRI site of pVK100. Then, it was further subcloned to use as an Enzyme A gene cassette. The 2.7 kb EcoRV fragment which includes ORF of Enzyme A gene with about 500 bp of non-coding regions at the both ends was excised from 3.4 kb NruI fragment, which was isolated from p24D4 in M13 mp18, and was ligated to HindIII site of pUC18 with HindIII linker (CAAGCTTG). The resulting plasmid was designated pSSA202. Enzyme A gene cassette (2.7 kb HindIII fragment) was then inserted at HindIII site of pVK102 to produce pSSA102R. The plasmid pSSA102R was introduced into nalidixic acid resistant *P. putida* [ATCC 21812]

by a conjugal mating method as described in Example 1-(1). The transconjugant of P. putida carrying pSSA102R was selected on MB agar medium containing 50 μg/ml nalidixic acid and 10 μg/ml tetracycline (MNT agar medium) and subjected to a mini-resting cell reaction. The reaction mixture (100 μl) consisting of 20 g/l L-sorbose, 3 g/l NaCl, 10 g/l CaCO$_3$ and the cells collected from the MNT agar culture with a toothpick was incubated at room temperature with gentle shaking for 24 hours. The reaction mixture was assayed with TLC and 2KGA was identified as the product, while no 2KGA was observed by the same resting cell reaction with the host, nalidixic acid resistant P. putida [ATCC 21812].

Enzyme B gene was originally cloned as a cosmid clone of pSS31 which has about 30 kb insert in SalI site of pVK102. It was subcloned as 6.5 kb BglII fragment into BglII site of pVK101 (ATCC 37157) to obtain pSSB102. Then, it was further subcloned to use as a Enzyme B gene cassette. The 6.5 kb BglII fragment was cloned into BamHI site of pUC18 to obtain pSSB202. Then, 2.3 kb XhoII fragment was excised from pSSB202. The 2.3 kb XhoII fragment includes ORF of Enzyme B with 120 bp of 5'-noncoding region and about 500 bp of 3'-noncoding region. The fragment was treated with Klenow fragment to fill-in the cohesive ends and cloned into HindIII site of pUC18 with HindIII linker to produce pSSB203. The Enzyme B gene cassette (2.3 kb HindIII fragment) was inserted at HindIII site of pVK102 to make pSSB103R. The plasmid pSSB103R was introduced into nalidixic acid resistant P. putida [ATCC 21812] by a conjugal mating method, and the transconjugant of P. putida carrying pSSB103R was selected on MNT agar medium and subjected to a mini-resting cell reaction. P. putida carrying pSSB103R showed the Enzyme B actiuvity (L-sorbose formation from D-sorbitol) in the resting cell reaction. (Incidentally, XhoII fragment was found not to be a XhoII-XhoII fragment, but a XhoII—XhoII fragment as a result of nucleotide sequencing. XhoI might be present in the XhoII preparation.)

Enzyme A' and Enzyme A" genes were originally cloned as a cosmid clone of p1E2 and p26C3 which have about 30 kb insert in SalI site of pVK102 and further subcloned basically as described above. Enzyme A' gene in 3.5 kb XhoII fragment was subcloned in BglII site of pVK102 to construct pSSA'101R, and Enzyme A" gene in 2.7 kb EcoRV fragment was first subcloned into M13mp19 and then re-subcloned between HindIII and BglII sites of pVK102 to construct pSSA"102.

Example 4

Isolation and Characterization of AADHs from Transconjugants of P. putida (1) Cultivation of Microorganisms P. putida [ATCC 21812] carrying cosmid vector pVK102 containing the Enzyme A, A', A" and B genes; pSSA102R, p1E2, p26C3 and pSSB103R, respectively, were cultivated in MB broth in the presence of antibiotic. Antibiotics added into medium were as follows; 5 μg/ml tetracycline for PSSA102R (Enzyme A) and PSSB 103R (Enzyme B), 25 μg/ml kanamycin for p1E2 (Enzyme A') and p26C3 (Enzyme A"). From the agar plate of MB containing the respective antibiotic, the cells were inoculated in 10 test tubes containing 5 ml MB medium with the respective antibiotic and cultivated with shaking at 30° C. After 2 days of cultivation, the cells were transferred to ten 500 ml-Erlenmeyer flasks containing 100 ml of the same medium and cultivated with shaking at 30° C. After 1 day of cultivation, the seed cultures were combined and transferred to 18 liters of the medium in 30 L jar fermenter (Marubishi) and cultivated for 18 hours with 300 rpm agitation and 1.0 vvm aeration at 30° C. The cells were harvested by centrifuge at 6,000×g for 10 minutes, washed once with 1.5 liters of 25 mM Tris-HCl, pH 7.5, containing 5 mM CaCl$_2$, 1 mM MgCl$_2$, 0.2 M NaCl, 2.5% sucrose, and 0.5 mM PMSF and stocked at −20° C. until use. As a result, about 150 g wet weight cells were obtained.

(2) Purification of the Cloned Enzymes A, A', A", and B.

Purifications of the Enzymes A, A', A" and B were carried out by the same procedure with almost the same scale. AU operations were carried out at 4–10° C. unless otherwise stated. The enzyme activity determination for Enzyme A, A', A" and B were carried out with the substrates, L-sorbose, n-propanol, n-propanol and D-glucose, respectively, by spectrophotometric assay as described in Example 1 throughout the purification steps. The cells (about 100 g wet weight cells containing 8–10 g of total proteins) were thawed and suspended in about 200 ml of 25 mM Tris-HCl, pH 8.0, and disrupted by passing through French press (1500 kg/cm$^2$) twice. Then, DNase and MgCl$_2$ were added to the suspension at the final concentration of 0.01 mg/ml and 1 mM, respectively, to reduce viscosity of the solution due to DNA. Cell debris was removed by centrifugation at 6,000×g for 10 minutes. The suspension was filled up to 240 ml with the 25 mM Tris-HCl buffer, pH 8.0, and centrifuged at 100,000×g for 90 minutes to remove insoluble membrane fraction. The soluble supernatant was filled up to 240 ml with the Tris buffer and, then, pyrroloquinoline quinone (PQQ) and CaCl$_2$ were added at the final concentration of 12.5 μM and 5 mM, respectively, and the solution was stirred vigorously for 15 minutes at room temperature. The soluble fraction prepared as above was fractionated by (NH$_4$)$_2$SO$_4$. The fraction 35–60%-saturated (NH$_4$)$_2$SO$_4$ was precipitated and resuspended in 100 ml of 25 mM Tris-HCl buffer, pH 8.0, containing 5 mM CaCl$_2$, and 5% sucrose and, then, PQQ was added again at the final concentration of 12.5 μM. The enzyme solution was dialyzed against 1000 ml of the same buffer (without PQQ) overnight. Twenty grams of solid polyethylene glycol #6000 was added to the dialysate slowly with gentle stirring. After stirring for 30 minutes, precipitates were removed by centrifugation at 10,000×g for 20 minutes, and the supernatant was filled up to 200 μml with the buffer indicated as above.

The enzyme solution prepared as above was purified by following three chromatography steps.

The First Step: DEAE-Toyopearl 650M

The crude enzyme solution was subjected to a column of DEAE-Toyopearl 650M (2.5×40 cm) which had been equilibrated with 25 mM Tris-HCl buffer, pH 8.0, containing 5 mM CaCl$_2$, and 5% sucrose. The column was washed with 400 ml of the same buffer and the enzyme was eluted by 2,000 ml of 0–0.5 M NaCl linear gradient in the buffer at a flow rate of 150 ml/hour. The enzyme active fractions were pooled and diluted 2-fold with the buffer without NaCl.

The Second Step: Q-Sepharose (Fast Flow)

The enzyme solution was subjected to a column of Q-Sepharose (Fast Flow) (1.5×20 cm) which had been equilibrated with the buffer without NaCl. The column was washed with 200 ml of the buffer containing 0.2 M NaCl and the enzyme was eluted by 600 ml of 0.2–0.6 M NaCl linear gradient in the buffer at a flow rate of 50 ml/hour. The enzyme active fractions were pooled and concentrated to 2.5 ml by using ultrafilter: Amicon, PM-30 under N$_2$ gas.

The Third Step: Sephacryl S-300 HR (gel filtration)

The concentrated enzyme was filtrated by a column of Sephacryl S-300 HR (2.5×100 cm) which had been equilibrated with 25 mM HEPES, pH 7.5, containing 5 mM $CaCl_2$, 5% sucrose, and 0.2 M NaCl. The column was developed by the same buffer at a flow rate of 20 ml/hour. The enzyme active fractions were pooled and concentrated to below 1 ml by the ultrafilter mentioned above and, then, stocked at −80° C. The enzymes concentrated in the HEPES buffer was stable for at least 2 months at −80° C.

Consequently, 26.0 mg of Enzyme A, 0.35 mg of Enzyme A', 0.41 mg of Enzyme A", and 5.0 mg of Enzyme B were obtained.

(3) Properties of the Enzymes A, A', A" and B.

a) Molecular Weight and Subunit.

The Enzymes A, A', A" and B were eluted at the same position from the same gel filtration column on Sephacryl S-300 under the same condition. The molecular weight of the enzymes was estimated as approximately 135,000 comparing with the molecular weight standard proteins (SDS-PAGE Standards, Low Range, Bio-Rad Laboratories, Richmond, Calif., USA). The Enzymes A, A', A" and B showed homogeneous single bands on SDS-PAGE analysis with molecular weights of 64,000, 62,500, 62,500 and 60,000, respectively. All the Enzyme bands A, A', A" and B were detected on Western blotting analysis using anti-AADH rabbit serum. Therefore, it was concluded that the enzymes consisted of two identical subunits as an homodimeric form.

b) N-terminal Amino Acid Sequence and Amino Acid Composition.

N-terminal amino acid sequences of the mature Enzymes A, A" and B were analyzed with automatic gas-phase sequencer (470A; Applied Biosystems) by Edman method [Acta Chem. Scand., 4, 283–293, {1950)]. The analysis of the Enzyme A' was not done because of an insufficient purity of the sample. The results were as follows:

Enzyme A: Gln-Val-Thr-Pro-Val-Thr - - -

Enzyme A": Blocked N-terminal residue

Enzyme B: Gln-Val-Thr-Pro-Ile-Thr-Asp-Glu-Leu-Leu-Ala - - - .

The determined sequences of Enzyme A and B were identical to the sequences (starting from the twenty-fourth residues) deduced from the nucleotide sequences described in SEQ ID NOS. 5 and 8; these results indicate that the initial 23 residues of the enzymes are the signal sequences. By analogy of the Enzymes A and B, the first 23 residues of Enzyme A' and A" are also deduced to be the signal sequences.

The amino acid composition of the Enzyme A was determined. The protein was hydrolyzed with 6 N HCl at 110° C. for 24 hours or 4 M methanesulfonic acid (after oxidation with performic acid) at 115° C. for 24 hours. Amino acid analysis was performed by using Kontron amino acid analyzer (ninhydrin system). The analytical data were compared with the amino acid composition deduced from the DNA sequence of Enzyme A gene. It indicated that the purified Enzyme A was certainly a product of the Enzyme A gene.

c) Substrate Specificity

The Enzymes A, A', A" and B were characterized by their substrate specificities on PMS-DCIP assay as described above using 8 substrates, n-propanol, isopropanol, D-glucose, D-sorbitol, L-sorbosone, D-mannitol, L-sorbose, and D-fructose. The results were indicated in Table 1.

d) Physicochemical Property

Physicochemnical studies of optimal pH, pH stability and thermal-stability, of the Enzymes A (as L-sorbose dehydrogenase activity), A' (as n-propanol dehydrogenase activity), A' (as L-sorbose dehydrogenase activity) and B (as D-sorbitol dehydrogenase activity), were performed by the PMS-DCIP assay.

Table 2 summarizes the results of optimal pH of the enzymes. The enzyme activity was assayed by the PMS-DCIP spectrophotometric assay using various pH buffers. The buffers were 50 mM Tris-malate-NaOH, pH 6.0, 6.5, 7.0, 7.5, 8.0 and 8.5; 50 mM glycine-NaOH, pH 9.0 and 9.5. The extinction coefficients of DCIP at pH 6.0, 6.5, 7.0, 7.5, 8.0, 8.5, 9.0 and 9.5 were taken as 10.8, 13.2, 14.5, 14.9, 15.0, 15.1, 15.1 and 15.1, respectively. All the enzymes showed their optimal points at pH 8.0–8.5. The Enzymes A" and B had relatively wide pH range toward lower pH, compared with the Enzymes A and A'.

Table 3 indicates the results of pH-stabilities of the enzymes. The enzyme (about 0.01 mg/ml) was incubated with 50 mM buffer containing 5% sucrose, 0.2 M NaCl, and 5 mM $CaCl_2$ at 25° C. for 3 hours and assayed by PMS-DCIP spectrophotometric method. The buffers were Na-acetate, pH4 and 5, Tris-malate-NaOH, pH 6, 7 and 8, glycine-NaOH, pH 9 and 10. The values in the table are expressed as relative activity against that obtained by no incubation at pH 8.0. The substrates used for the enzymes were 125 mM L-sorbose for Enzymes A and A', 50 mM n-propanol for Enzyme A', and 125 mM D-sorbitol for Enzyme B. Profiles of pH-stabilities of Enzymes A, A', A", and B were almost the same; they were stable at the range of pH 6 to 9.

Table 4 indicates the results of thermal-stabilities of the enzymes. The enzyme (about 0.05 mg/ml) in 25 mM HEPES buffer, pH 7.5, containing 5% sucrose, 0.2 M NaCl, and 5 mM $CaCl_2$ was incubated at temperature indicated in the table (4–60° C.) for 5 minutes, cooled in ice bath and assayed by PMS-DCIP spectrophotometric method. Remaining activity was expressed as relative activity against that obtained by 4° C. incubation. The substrates used for the enzymes were 125 mM L-sorbose for Enzyme A and Enzyme A', 50 mM n-propanol for Enzyme A', and 125 mM D-sorbitol for Enzyme B. After the treatment of the enzymes at 40° C. for 5 min, the residual activity of Enzyme A was 20%, and those of Enzymes A', A", and B were 70–85%.

e) General Inhibitors

The enzyme (about 0.05 mg/ml) in 25 mM HEPES buffer, pH 7.5, containing 5% sucrose was incubated with metal or inhibitor for 30 minutes at 25° C. Remaining activity was assayed by PMS-DCIP spectrophotometric assay as described in Example 1. Remaining activity is expressed as relative activity against blank incubation. Effects of metal ions on the enzymes are listed in Table 5. $MgCl_2$ and $CaCl_2$ were nearly inert to the enzymes, while the other metal ions, especially $CuCl_2$, significantly affected. Effects of inhibitors on the enzymes are also included in Table 5. EGTA and EDTA inhibited the Enzyme A, A' and A", remarkably. However, Enzyme B was less inhibited than the A group enzymes by EDTA and EGTA.

Example 5

Efficient Production of Enzyme B in *E. coli*

The signal peptide region of the Enzyme B was replaced with that of maltose binding protein (malE) of *E. coli* as follows. Two oligonucleotides (SEQ ID NOS. 9 and 10) were synthesized with Applied Biosystem 381A DNA synthesizer and annealed to generate a double-stranded DNA fragment encoding a amino acid sequence (SEQ ID NO. 11), MetLysIleLysThrGlyAlaArg-IleLeuAlaLeuSerAlaLeuThrThrMetMetPheSer AlaSerAlaLeuAla(Gln), which was, then, treated with T4 polynucleotide kinase [J. Biol. Chem., 259, 10606–10613, (1984)]. pSSB203 (see Example 3) was digested with the restriction enzyme SphI, treated with T4 DNA polymerase and digested with BstP1. The resulting 1.72 kb DNA fragment carrying Enzyme B gene without the region coding for the original signal sequence and the first amino acid residue (Gln) of the mature Enzyme B was isolated from an agarose gel after agarose gel electrophoresis. The *E. coli* expression vector, pTrc99 A (Pharmacia Co., Uppsala, Sweden), which was digested with the restriction enzymes NcoI (at ATG start codon) and SmaI was ligated with above two DNA fragments. The resulting plasmid was designated as pTrcMal-EnzB and used to transform *E. coli* JM109. The transformant was grown in two 2-liter flasks each containing 600 ml of LB with 100 μg/ml ampicillin at 28° C. and IPTG was added to 0.1 mM when cell concentration reached at about 1.5 OD600. Following the addition of IPTG, the cells were cultivated for an additional 3–4 hours. The cells were harvested by centrifugation (4,000×g) at 25° C. for 10 minutes, suspended with 500 ml of 30 mM Tris-HCl, pH 8.0, containing 20% sucrose at 25° C. After EDTA was added to 1 mM into the cell suspension, the cells were incubated with gentle shaking for 5 minutes at 25° C. and collected by centrifugation (8,000×g) at 4° C. for 15 minutes. The cells were resuspended with 500 ml of ice cold 5 mM $MgSO_4$ solution and incubated with gentle shaking for 5 minutes at 4° C. The cell suspension was centrifuged at 8,000×g for 10 minutes at 4° C. to obtain a supernatant as a cold osmotic shock extract, which was found to contain the Enzyme B protein (a molecular weight of 60,000) with the purity more than 50–60% by SDS-PAGE analysis. The supernatant was first supplemented with Tris-HCl, pH 8.0, to 20 mM, and incubated at 25° C. firstly with EDTA at 10 mM final concentration for 10 min, secondly with $CaCl_2$ at 20 mM final concentration for 10 minutes and lastly with PQQ at 25μM final concentration. For stabilization of the enzyme, α-methyl-D-glucoside (a competitive inhibitor) was added to 20 mM final concentration in the supernatant. The Enzyme B was completely purified by following two chromatographies. At first, the supernatant was loaded onto a Q-Sepharose column (1.6×12 cm) which had been equilibrated with 20 mM Tris-HCl, pH 8.0, containing 1 mM $CaCl_2$ and 20 MM α-methyl-D-glucoside, and the Enzyme B was eluted with 600 ml of 0–0.4 M NaCl linear gradient in the same buffer. A red protein peak eluted at about 0.25 M NaCl was collected and concentrated to about 0.5 ml by Centricon-30 (Amicon). Finally, the Enzyme B was passed through a SephacrylS-300 HR column with 20 mM HEPES, pH 7.8, containing 0.2 M NaCl, 1 mM $CaCl_2$ and 20 mM α-methyl-D-glucoside. A red protein peak eluted around a molecular weight of 135,000 daltons position was collected as the final purified Enzyme B. Consequently, about 8 mg of the purified Enzyme B was obtained from 1.2 liters cultivation broth of *E. coli*.

Example 6

Host-vector System

A host-vector system for *G. oxydans* [DSM No. 4025] was established by using the conjugal mating system with a broad-host-range cosmid, pVK102. Initially, only one transconjugant was isolated from *G. oxydans* [DSM No. 4025] having nalidixic acid resistance. A new host, GOS2, was isolated from the transconjugants, *G. oxydans*[DSM No. 4025] carrying pVK102 by curing pVK102. A second host, GOS2R, was then derived from the GOS2 by adding rifampicin resistance (100 μg/ml), which enables easy selection of the transconjugants from the donor *E. coli*. The plasmid transfer frequency into GOS2R was $10^{-3} \sim 10^{-4}$ transconjugants/recipient The 2KGA productivity of GOS2R, however, was about 10% lower than that of *G. oxydans* [DSM No. 4025]. The third host, GORS635, was obtained from *G. oxydans* [DSM No. 4025] by selecting the strain with rifampicin resistance, high 2KGA productivity and relatively high competence through a series of experiments, including the conjugation, curing and 2KGA fermentation.

(1) Isolation of GOS2

Resistance to nalidixic acid was added to *G. oxydans* [DSM No. 4025]. Cells of *G. oxydans* [DSM No. 4025] were streaked onto Trypticase Soy Broth (BBL, Becton Dickinson Microbiology Systems Cockeysville, Md. USA) (T) agar medium with 50 μg/ml of nalidixic acid (IN agar medium) and incubated at 27° C. for 5 days. The resulting colonies were again streaked on the same agar plates to obtain a nalidixic acid-resistant *G. oxydans* DSM No. 4025, GON. The broad-host-range cosmid pVK102 ($Km^r$, $Tc^r$) was transferred from *E. coli* carrying pVK102 into the GON strain by the tri-parental conjugal mating as follows. A helper strain, *E. coli* carrying pRK2013 and a donor strain carrying pVK102 were cultivated in LB medium with 50 μg/ml of kanamycin at 37° C. overnight. The cultures were transferred to fresh LB medium with kanamycin and incubated for 5–6 hours. Recipient strain, GON, was cultivated in TN liquid medium at 30° C. overnight. *E. coli* and GON strains were separately centrifuged and re-suspended in equal- and one tenth-volume of fresh T medium, respectively. One hundred μl of each cell suspension was mixed together and 30 μl portion of the mixture was spotted onto a nitrocellulose filter placed on the surface of a NS2 agar plate. Transconjugants were selected on the T agar medium containing 50 μg/ml of nalidixic acid and 50 μg/ml of kanamycin (TNK agar medium). Several colonies were obtained on the selection plates where many spontaneous mutants of *E. coli* ($Nal^r$, $Km^r$) colonies also appeared. The plasmid and chromosomal DNAs of the transconjugant candidates were prepared and compared with the authentic pVK102 and chromosomal DNA of *G. oxydans* DSM No. 4025 by restriction analysis and Southern-blot hybridization. Consequently, one transconjugant of *G. oxydans* [DSM No. 4025] carrying pVK102, GON8-1, was identified. The plasmid DNA prepared from GON8-1 was identical to that of pVK102 and replicable in *E. coli*. The chromosomal DNA of GON8-1 was identical to that of *G. oaxdans* [DSM No. 4025].

To isolate strains that could work as hosts with higher competence for conjugal mating, the transconjugant GON8-1 was cured of the plasmid pVK102. GON8-1 was cultivated in T broth without antibiotics at 30° C. for 2 days, 2% of the culture was transferred into fresh T broth. After three such cultivation cycles, the cells were spread on T agar plates, incubated at 27° C. for 4 days, and the resulting colonies were picked onto TNK and TN agar plates to select $Km^s$ strains. One of the $Km^s$ strains was designated as GOS2 and was confirmed by Southern-blot hybridization not to be carrying any DNA region of pVK102. Then, pVK102 was transferred into strain GOS2 by a conjugal mating; this strain showed $10^2 \sim 10^3$ fold higher competence (namely $10^{-5} \sim 10^{-6}$ transconjugants/recipient) than *G. oxydans* [DSM No. 4025] did.

(2) Isolation of GOS2R, a Rifampicin-resistant Mutant of GOS2.

Rifampicin resistant ($Rif^r$) mutants from GOS2 were isolated through repeated transfer of GOS2 cells onto T agar medium containing 20~100 μg/ml rifampicin; one of the $Rif^r$ strains was designated as GOS2R. Strain GOS2R showed very high competence; $10^{-2} \sim 10^{-3}$ and $10^{-4}$ transconjugants/recipient on TRK agar (T agar medium containing 100 µg/ml rifampicin and 50 µg/ml kanamycin) plate and on TRT agar (T agar medium containing 100 µg/ml rifampicin and 3 µg/ml tetracycline) plate, respectively.

2KGA productivity from L-sorbose by GOS2R was compared with that of G. oxydans [DSM No. 4025]. The cells maintained on NS2 agar medium were inoculated into 5 ml of the seed culture medium consisting of 8% L-sorbose (sterilized separtely), 0.05% glycerol, 0.25% $MgSO_4.7H_2O$, 1.75% corn steep liquor, 5.0% baker's yeast, 1.5% $CaCO_3$, and 0.5% urea (sterilized separately) (pH 7.0 before sterilization) and incubated at 30° C. for 24 hours. The resulting seed culture (5 ml) was inoculated into a 500 ml Erlenmeyer flask containing 50 ml of the production medium PMS10 consisting of 10% L-sorbose, (sterilized separtely), 0.05% glycerol, 0.25% $MgSO_4.7H_2O$, 3% corn steep liquor, 6.25% baker's yeast, 1.5% $CaCO_3$, and 1.6% urea (sterilized separately) (pH 7.5 before sterilization) and incubated at 30° C. for 4 days with shaking (180 rpm). The quantitative determination of 2KGA was assayed by high performance liquid chromatography. GOS2R and G. oxydans [DSM No. 4025] produced 87.3 and 97.3 g/l of 2KGA, respectively.

(3) Isolation of GORS6–35 as a Host With High 2KGA Productivity

To evaluate the self-cloning of AADH genes in the strain with the same productivity of 2KGA from L-sorbose as G. oxydans [DSM No. 4025], a new host was constructed by (i) adding rifampicin-resistance (200 µg/ml), (ii) introducing and curing pVK102, and (iii) selecting 2KGA high producer from L-sorbose. Thus obtained GORS635 shows the following two characteristics: (i) almost the same 2KGA productivity (about 100 g/l 2KGA from 10% L-sorbose) as the parent G. oxydans [DSM No. 4025]; and (ii) a competence ($10^{-6}$~$10^{-7}$ transconjugants/recipient).

Example 7

Construction of Promoter-eplaced Enzyme B Gene

Figure 10:
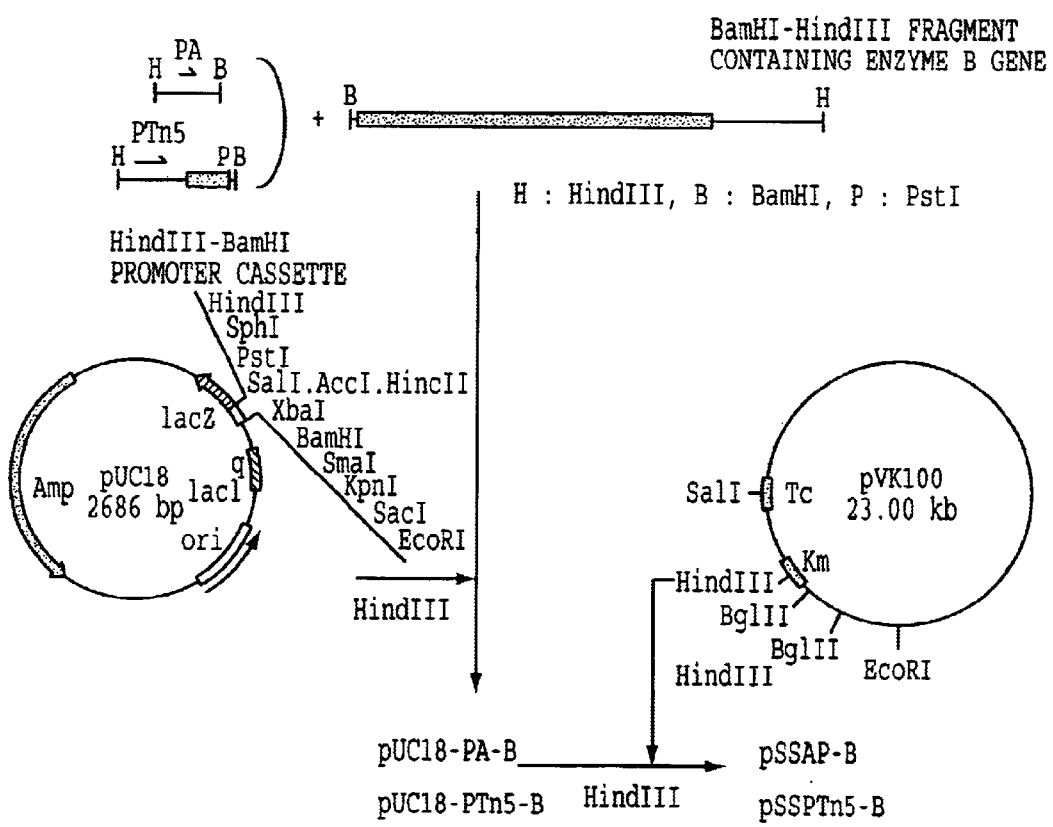
FIG. 10 illustrates a scheme of the replacement of the promoter for the Enzyme B gene.

The promoter of Enzyme A gene (PA) is likely strong in G. oxydans [DSM No. 4025] because Enzyme A was found to be one of the highest-expressing proteins in amount in the cell when total cell free extract of G. oxydans [DSM No. 4025] was subjected to SDS-polyacrylamide gel electrophoresis and the resulting gel was stained with Coomassie Brilliant Blue R-250. The PA and another promoter, a promoter of kanamycin resistant gene of Tn5 (PTn5), which could express the kanamycin resistance in G. oxydans [DSM No. 40251], were attached to the structure gene with the SD sequence of Enzyme B gene as shown in FIG. 10.

Figure 9:
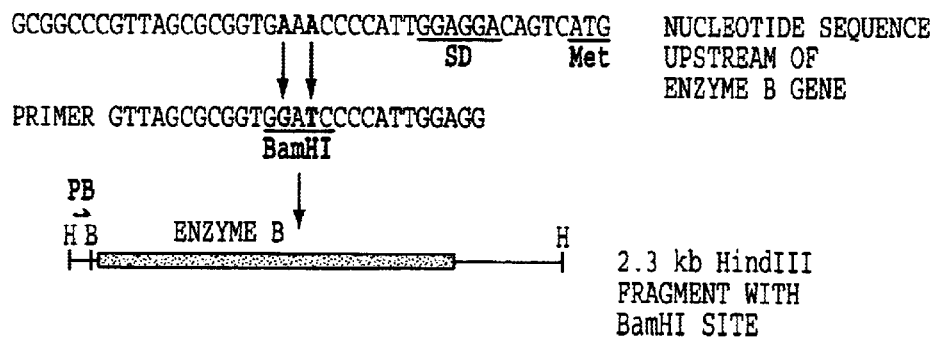
FIG. 9 shows a site-directed mutagenesis to introduce a BamHI site upstream of the Enzyme B gene.

Enzyme B gene-containing 2.3 kb HindIII fragment was inserted in M13 mp 18 and the resulting phage DNA was subjected to site-directed mutagenesis carried out with T7-GEN™ In Vitro Mutagenesis Kit (TOYOBO Co., Ltd., Osaka Japan) according to the recommendations by the supplier (FIG. 9). To insert various promoters upstream of Enzyme B gene instead of Enzyme B promoter, BamHI site was created upstream of the SD sequence. A primer for the mutagenesis, GTTAGCGCGGTGGATCCCCATTGGAGG (27-mer including BamHI site, SEQ-IDNo. 12), were synthesized with Applied Biosystems 381A DNA synthesizer. The resulting BamHI-HindIII fragment carries Enzyme B SD and structural genes without the Enzyme B promoter (PB).

Then promoter of Enzyme A gene (PA) was subcloned by PCR method using primers tagged with the sequences for the HindIII and BamHI sites. The PCR reaction was carried out with GeneAmp™ DNA Amplification Reagent Kit (Takara Shuzo, Kyoto, Japan) with a thermal cycler, Zymoreactor II (Atto Corp., Tokyo, Japan). The reaction consists of pre-treatment before adding enzyme (94° C., 5 minutes.); 30 cycles of denaturation step (94° C., 1 minute.), annealing step (60° C., 1 minute.), and synthesis step (72° C., 1 minute.); and post-treatment (72° C., 5 minutes.). Plasmid pSSA202 (pUC18-Enzyme A gene in 2.7 kb HindIII was used as the template DNA. The reaction mixture contained 200 µM of dNTPs, 1 µM of each primer, 1 ng of template DNA and 2.5 u of AmpliTaq™ DNA polymerase in the buffer supplied. Consequently, 300 bp fragment upstream from the SD sequence was amplified. The PCR product was inserted into pUC18 between HindIII and BamHI sites and used for nucleotide sequencing; the amplified sequences do not have any mutations caused by misincorporation in PCR.

The promoter of the kanamycin resistant gene, PTn5, was first obtained as a HindIII-PstI fragment from the plasmid pNeo (Pharmacia Co., Uppsala, Sweden). The HindIII-PstI fragment was then inserted into the multicloning site of pUC18, and finally the PTn5 was excised as a HindIII-BamHI fragment.

The HindIII-BamHI fragments containing the PA and PTn5 promoters were inserted in the HindIII site of pUC18 together with BamHI-HindIII fragment containing the PB promoter-removed Enzyme B structural gene. The HindIII fragments from the resulting plasmids were subcloned into pVK100 to produce pSSAP-B and pSSPTn5-B, which were transferred into GOS2R by conjugal mating as described in Example 6.

Example 8

2KGA Production by Transconjugants of GOS2R in Flask (1) 2KGA Production From L-sorbose by Enzyme-A Gene-amplified Transconjugant in Single Culture Fermentation in Flask.

The Enzyme A plasmid, pSSA102R, and the vector plasmid, pVK102, were introduced into GOS2R by a conjugal mating method as described in Example 6. The resulting transconjugants were maintained on NS2 agar medium containing 30 µg/ml tetracycline and subjected to 2KGA fermentation from L-sorbose. The cells of the transconjugants were inoculated into 5 ml of the seed culture medium described in Example 6 and incubated at 30° C. for 24 hours. The resulting seed culture (5 ml) was inoculated into a 500-ml Erlenmeyer flask containing 50 ml of the PMS10 production medium described in Example 6 or the PMS12 production medium consisting of 12% L-sorbose, (sterilized separtely), 0.05% glycerol, 0.25% $MgSO_4.7H2O$, 3% corn steep liquor, 10% baker's yeast, 1.5% $CaCO_3$, and 2% urea (sterilized separately) (pH 7.5 before sterilization) and incubated at 30° C. for 4 or 5 days with shaking (180 rpm). As a result, GOS2R (pSSA102R) and GOS2R (pVK102) produced 92.2 and 89.1 g/l 2KGA, respectively, from 10% L-sorbose in 4 days, and 105.7 and 99.9 g/l 2KGA, respectively, from 12% L-sorbose in 5 days.

(2) 2KGA Production from D-sorbitol by GOS2R (pSSB 103R) in Single Culture Fermentation in Flask.

The Enzyme B plasmid, pSSB103R, and the vector plasmid, pVK102, were introduced into GOS2R by a conjugal mating method as described in Example 6. The resulting transconjugants were maintained on NS2 agar medium containing 30 µg/ml tetracycline and subjected to 2KGA fermentation from D-sorbitol. The cells of the transconjugants were inoculated into 5 ml of the seed culture medium consisting of 8% D-sorbitol, 0.05% glycerol, 0.25% $MgSO_4.7H_2O$, 1.75% corn steep liquor, 5.0% baker's yeast, 1.5% $CaCO_3$, and 0.5% urea (sterilized separately) (pH 7.0 before sterilization) and incubated at 30° C. for 24 hours. The resulting seed culture (5 ml) was inoculated into a 500-ml Erlenmeyer flask containing 50 ml of three production media shown in Table 8 and incubated at 30° C. for 3 days with shaking (180 rpm). As a result, GOS2R (PSSB103R) produced about 61.5, 71.5 and 73.0 g/l of 2KGA from 8%, 10% and 12% D-sorbitol, respectively, while GOS2R (pVK102) produced 19.5, 25.4 and 30.2 g/l 2KGA, respectively.

TABLE 8

| Ingredients | PMSL8 | PMSL10 | (%) PMSL12 |
| --- | --- | --- | --- |
| D-Sorbitol | 8.0 | 10.0 | 12.0 |
| Glycerol | 0.05 | 0.05 | 0.05 |
| $MgSO_4.7H_2O$ | 0.25 | 0.25 | 0.25 |
| CSL | 3.0 | 3.0 | 3.0 |
| Baker's yeast | 5.0 | 6.25 | 10 |
| Urea* | 1.25 | 1.6 | 2.0 |
| $CaCO_3$ | 1.5 | 1.5 | 1.5 | pH 7.5 before sterilization
*sterilized separately (3) 2KGA Production from D-sorbitol by GOS2R (pSSAP-B) and GOS2R (pSSPTn5-B) in Single Culture Fermentation in Flask.

The cells of GOS2R (pSSAP-B), GOS2R (pSSPTn5-B) and GOS2R (pSSB 103R), GOS2R (pVK100) were cultivated in the PMSL10 production medium in Erlenmeyer flasks at 30° C. for 3 days as described in Example 8 (2). The amounts of 2KGA produced were shown in Table 9.

TABLE 9

| | The amount of 2KGA (g/l) | | |
| --- | --- | --- | --- |
| Strain | 1 day | 2 days | 3 days |
| GOS2R (pSSAP-B) | 47.2 | 67.0 | 67.7 |
| GOS2R (pSSPTn5-B) | 23.4 | 28.6 | 29.4 |
| GOS2R (pSSB103R) | 30.5 | 54.3 | 62.7 |
| GOS2R (pVK100) | 10.2 | 18.3 | 19.3 |
| GOS2R | 6.7 | 14.7 | 16.4 |

Example 9

2KGA Production from D-sorbitol in 3-L Jar Fermentations by Single Microorganism (1) Single Culture Fermentation by GOS2R (pSSB103R)

Five ml portions of the seed culture prepared in test tubes as described in Example 8-(2) were transferred to four 500-ml Erlenmeyer flasks containing 50 ml of the same seed culture medium and incubated at 30° C. for 24 hours with shaking (180 rpm). The resulting broth (200 ml of the seed culture) was inoculated into 3-L jar fermentor containing 1800 ml of the PMSL10 production medium containing 3 ml of antifoam. The fermentor was operated at 30° C., 700 rpm and 0.5 vvm. D-Sorbitol was fed in ways: (i) 200 ml of 50% D-sorbitol was fed in 6 hours from the $24^{th}$ to the $30^{th}$ hour; or (ii) 280 ml of 50% D-sorbitol was fed in 8.3 hours from the $24^{th}$ to the $32.3^{th}$ hour. As a result, 99.0 and 103.4 g/l 2KGA were produced by the fed-batch fermentations (i) and (ii), respectively in 51 hours.

Example 10

2KGA Production from D-sorbitol by Enzyme B Gene-amplified GOS2R in Mixed Culture Fermentation With E. coli in Flask (1) Mixed-culture Fermentations With B. Megaterium, E. coli and P. putida.

B. megaterium [DSM No. 4026], E. coli HB101 and P. putida [ATCC 21812], growth factor suppliers, were cultivated in 150 ml of the seed culture medium consisting of 0.3% yeast extract (Difco), 0.3% beef extract (Kyokuto Seiyaku, Tokyo, Japan), 3% corn steep liquor, 1% polypeptone (Kyokuto), 0.1% urea, 0.1% $KH_2PO_4$, 0.02% $MgSO_4.7H_2O$, 2% L-sorbose, 0.1% $CaCO_3$ (pH 7.1 before sterilization) for 24 hours at 37, 37, and 30° C., respectively. Strain GOS2R (pSSB103R) was cultivated in two test tubes containing 5 ml of the seed culture medium as described in Example 8-(2) at 30° C. for 24 hours. Four ml of GOS2R (PSSB 103R) seed cultures and 3.5 ml of growth factor supplier seed culture were inoculated to a 500-ml of Erlenmeyer-flask containing 50 ml of the production medium for mixed culture fermentations consisting of 8% D-sorbitol, 0.01% $MgSO_4.7H_2O$, 1% corn steep liquor, 0.1% $KH_2PO_4$, 0.6% $CaCO_3$, 1.5% urea (sterilized separately) and antifoam (one drop per flask) (pH 7.0 before sterilization) and the flask was shaken at 30° C. for 46.5 hours. As a result, mixed culture with B. megaterium DSM No. 4026, E. coli HB 101 and P. putida ATCC 21812 produced 49.9, 54.1, 31.3 g/l 2KGA, respectively.

(2) Mixed Culture Fermentation of GOS2R (pSSAP-B) With E. coli in Flask.

Mixed culture fermentations by GOS2R (pSSAP-B) with E. coli was performed in the same manner as described above except for the seed culture medium for E. coli containing 2% D-sorbitol instead of 2% L-sorbose. From 10% of D-sorbitol, GOS2R (pSSAP-B) produced 73.7 g/l 2KGA in 48.5 hours.

Example 11

2KGA Production by Recombinant AADH

A reaction mixture containing 1.7 mg/ml of purified Enzyme A (purified according to Example 4), 50 mM Tris-HCl, pH 7.5, 5 mM $CaCl_2$, 8 mg/ml bovine serum albumine (BSA), 1 mM PMS, 20 µg/ml PQQ, and 4% L-sorbose was incubated at 30° C. with gentle shaking for 20 hours. As a result, about 2 g/l 2KGA (TLC assay) was produced.

The other reaction mixture containing 2.4 mg/ml each of purified Enzyme A and Enzyme B (purified according to Example 4), 50 mM Tris-HCl, pH7.5, 5 mM $CaCl_2$, 8 mg/ml BSA, 1 mM PMS, 20 µg/ml PQQ, and 2% D-sorbitol was incubated at 30° C. with gentle shaking for 20 hours. As a result, 0.25 g/l 2KGA (HPLC assay) and about 5 g/l L-sorbose (TLC assay) were produced.

Example 12

Production of Aldehydes from Alcohos Ketones From Alcohols or Carboxylic Aicds and Carboxylic Acids from Aldehydes Enzyme reactions with purified Enzyme A or Enzyme B and various substrates were performed as described in Example 11. The resulting products were identified by TLC and/or HPLC as shown in Table 10.

TABLE 10

| Enzyme | Substrate | Product |
|---|---|---|
| Enzyme A | D-Sorbitol | D-Glucose, L-Gulose |
|  | L-Sorbose | L-Sorbosone, 2KGA |
|  | L-Sorbosone | 2KGA |
|  | D-Mannitol | D-Mannose |
|  | D-Fructose | 2KD |
| Enzyme B | D-Glucose | D-Gluconic acid |
|  | D-Sorbitol | L-Sorbose |
|  | L-Sorbosone | 2KGA |
|  | D-Mannitol | D-Fructose |
|  | L-Idose | L-Idonic acid |
|  | Glycerol | Dihydroxyacetone |
|  | D-Gluconic acid | 5-Keto-D-gluconic acid |
|  | D-Mannoic acid | 5-Keto-D-mannoic acid |

Enzyme A converted D-fructose to 2KD; this means that D-glucosone was also a product formed from D-fructose as the intermediate.

Example 13

2KGA and L-sorbose Production by a Transconjugant of P. putida

A resting cell mixture (2 ml) containing 1% $CaCO_3$, 0.3% NaCl, 1 mM PMS, 5 µg/ml PQQ, 2% L-sorbose and 10 OD600 unit-cells of nalidixic acid resistant ($Nal^r$) P. putida [ATCC 21812] carrying pSSA102R or pVK100 was incubated at 30° C. with gentle shaking for 17 hours. As a result, $Nal^r$ P. putida [ATCC 21812] carrying pSSA102R or pVK100 produced 18.9 or 0.0 g/l of 2KGA, respectively.

A resting cell mixture (2 ml) containing 1% $CaCO_3$, 0.3% NaCl, 1 mM PMS, 5 µg/ml PQQ, 2% [sorbitol and 10 OD600 unit-cells of $Nal^r$ P. putida [ATCC 21812] with pSSB103R or with pVK100 was incubated at 30° C. with gentle shaking for 17 hours. As a result, $Nal^r$ P. putida (ATCC 21812] carrying PSSB103R or with pVK100produced 7.8 or 0.0 g/l of L-sorbose, respectively.

Example 14

Construction and Characterization of Chimera AADH Enzymes (1) Construction of Chimera AADH Enzymes To alternate substrate specificity of AADH enzymes, a variety of chimera enzymes between Enzymes A and B were constructed.

Figure 2:
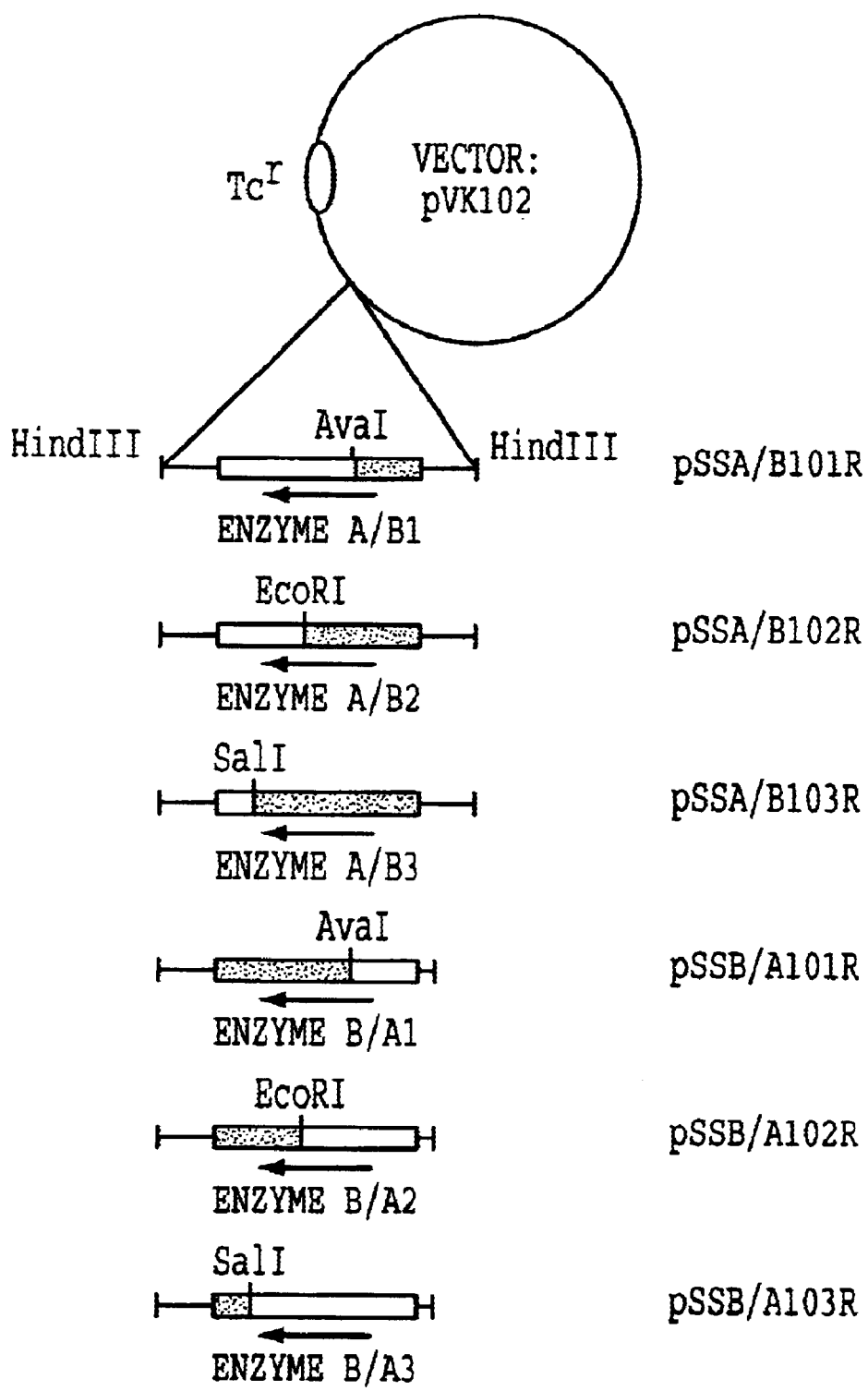
FIG. 2 schematically illustrates the structures of recombinant expression vectors each carrying a recombinant DNA molecule which encodes a chimeric enzyme of the present invention.

(i) FIG. 2 shows the structure of the chimera genes by strategy I (restriction and ligation method). The restriction sites conserved in both genes, Ava I (nucleotide No. 603 of Enzyme A gene), EcoRI site (nucleotide No. 1084), and SalI site (nucleotide No. 1470) (FIG. 7) were used for the construction. First, Enzyme A and B gene cassettes (2.7 kb and 2.3 kb Hind III fragments, respectively) were subcloned in the same direction in this order on pUC18 to produce the plasmid pSSAB201, and Enzyme B and A gene cassettes were also subcloned in the same direction in this order on pUC18 to produce pSSBA201 (FIG. 3). After partial digestion of these plasmids with each restriction enzyme, resulting digests were ligated and used to transform E. coli JM109. Ampicillin resistant transformants were analyzed for their plasmids, and Enzyme A gene-headed and Enzyme B-headed chimera gene cassettes with the expected HindIII fragment size of 2.7 kb and 2.3 kb, respectively, were selected. Thus constructed chimera gene cassettes were introduced into HindIII site of pVK102 to produce pSSA/B101R, pSSA/B102R, pSSA/B103R, pSSB/A101R, pSSB/A102R, and pSSB/A103R which encode Enzyme A/B1, EnzymeA/B2, EnzymeA/B3, EnzymeB/A1, EnzymeB/A2, and EnzymeB/A3, respectively, as shown in FIG. 2. These six plasmids were introduced into Nalr P. putida by a conjugal mating method as described in Example 1.

Figure 7:
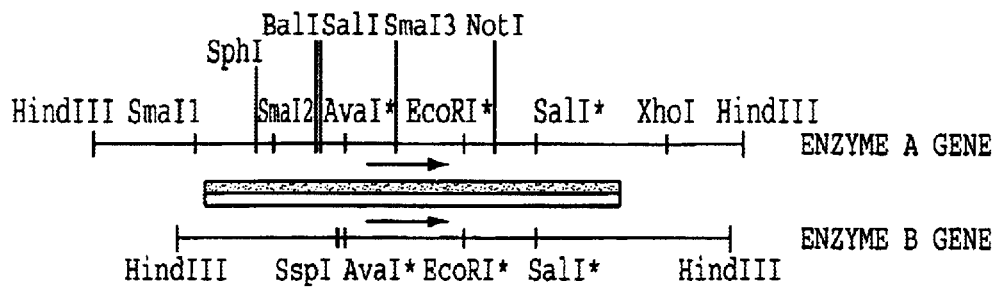
FIG. 7 shows the restriction map of the genes of Enzymes A and B.

(ii) FIG. 8 shows the scheme for constructing chimera genes by strategy II; in vivo homologous recombination method to construct chimeras recombinated at random positions for altering the substrate specificity of AADH enzymes. The principle of this method is as follows: (i) Locate two homologous genes to be recombinated tandem in one plasmid with selective marker; (ii) Cut it at restriction sites between the two genes, and transform rec $A^+$ E. coli cell with the linearized plasmid; (iii) Select transformants showing selective marker which carry circularized DNAs by recombination between the two genes at various positions. Two plasmids pSSAB201 and pSSBA201 which have Enzyme A and Enzyme B genes on pUC18 (FIG. 3) were linearized with pairs of restriction enzymes as shown in FIG. 8. E. coli JM101(rec $A^+$) was transformed with these linearized DNAs. Transformants were obtained at frequency of $10^1$–$10^2$ /µg DNA. To begin with, DNA size was determined to remove illegitimate recombinants. As a result, correct recombinants were obtained at ratio of 30%. XhoI-BalI fragment in which Enzyme A gene lost about two-third of C-terminus was efficient to obtain chimeras recombinated within one-third of N-terminus. Next, the recombinants were classified into recombination site groups bordered by restriction sites of three SmaI, SphI, SalI and BalI (FIG. 7). Thus constructed chimera genes were subcloned on pVK100 as HindIII cassette and the plasmids were introduced into $Nal^r$ P. putida by a conjugal mating method.

Figure 11:
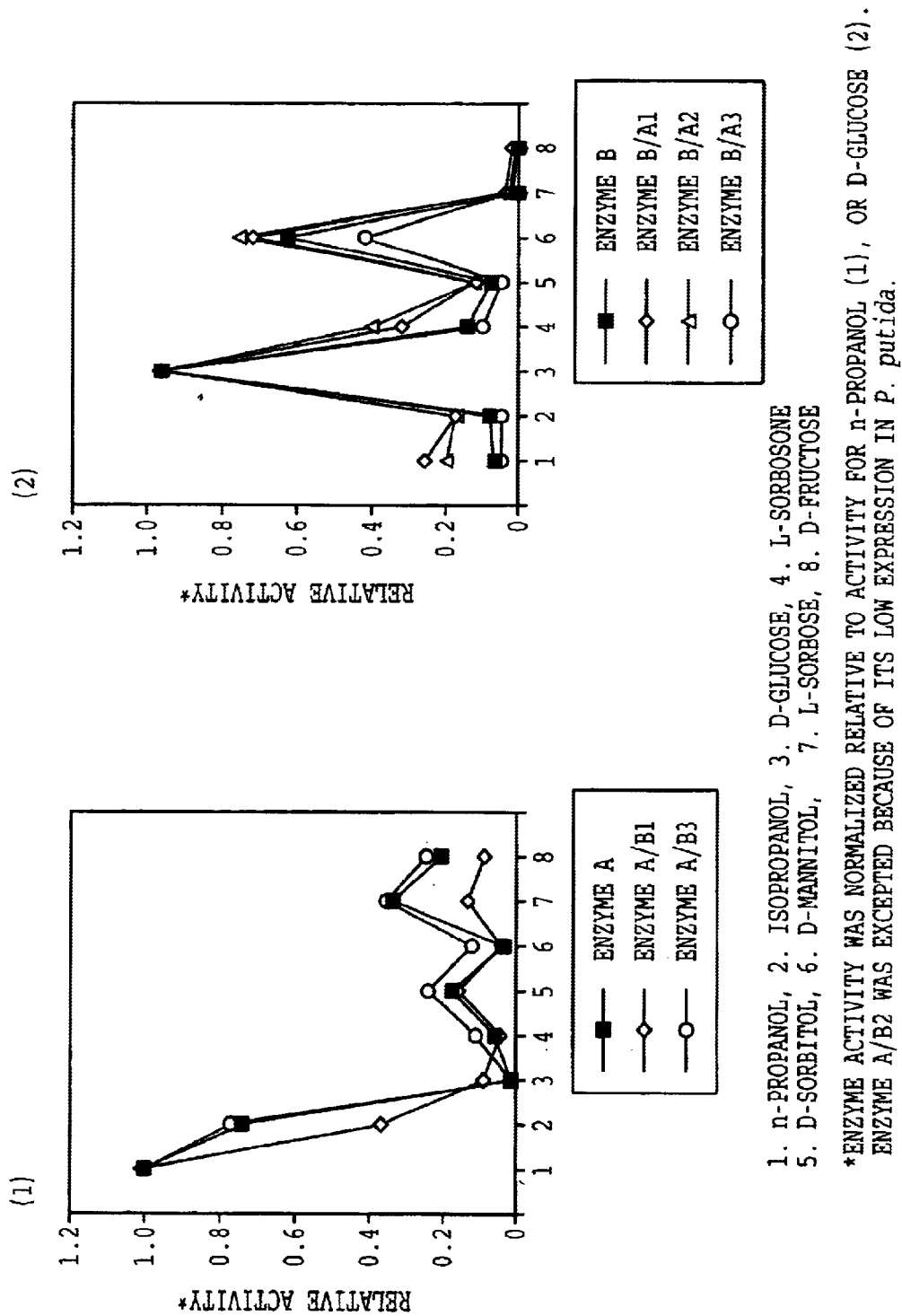
FIG. 11 shows graphs illustrating the substrate specificity of chimeric enzymes of the invention.

(2) Characterization of Chimera AADH Enzymes (i) Characteristics of the chimeras obtained by restriction and ligation method The chimera enzymes expressed in $Nal^r$ P. putida were characterized enzymatically by using soluble fractions of the cells of the transconjugants as described in Example 1. Eight substrates were used for the evaluation as shown in FIG. 11. Enzymes A/B1 and A/B3 showed Enzyme A-type substrate specificity, although their expression level was lower than that of Enzyme A. On the other hand, Enzymes B/A1, B/A2, and B/A3 showed Enzyme B-type substrate specificity, although activity on n-propanol (Enzyme A type activity) became higher in accordance with the increase of the region from Enzyme A; the expression level of Enzyme B/A1 gene was about 2-fold higher than that of wild Enzyme B gene. As a result from the chimeras obtained by recombination and ligation method, it was concluded that the N-terminal one third region of Enzyme A or Enzyme B primarily determines its substrate specificity.

(ii) Characteristics of the chimeras obtained by homologous recombination method.

Among the chimeras obtained as above, seven out of eighteen chimera enzymes obtained from the chimera genes recombined between SmaI2 and SalI sites illustrated in FIG. 7 showed preferable substrate specificity. The seven chimera enzymes converted D-sorbitol to L-sorbose, not to D-glucose produced by Enzyme A, and converted L-sorbose to 2KGA like Enzyme A. The recombination sites were determined by nucleotide sequencing as described in Example 2. These type of chimeras have an approximate structure of "N-terminal 2/9 of Enzyme A+C-terminal 7/9 of Enzyme B" was classified as Enzyme superA-type. There were three Enzyme superA-type enzymes according to the recombinated site: Enzyme A/B21 (chimera consisting of Enzyme A amino acid residue Nos. 1–128 and Enzyme B amino acid residue Nos. 129–556), Enzyme A/B22 (chimera consisting of Enzyme A amino acid residue Nos. 1–125 and Enzyme B amino acid residue Nos. 126–556) and Enzyme A/B25 (chimera consisting of Enzyme A amino acid residue Nos. 1–135 and Enzyme B amino acid residue Nos. 136–556). *P. putida* transconjugant expressing genes of Enzyme A/B21, Enzyme A/B22 or Enzyme A/B25 converted D-sorbitol to L-sorbose and did not convert D-sorbitol to D-glucose. The other type of chimera Enzyme A/B31 (Enzyme A amino acid residue Nos. 1–95 and Enzyme B amino acid residue Nos. 96–556) converted D-sorbitol to L-sorbose efficiently and did not convert L-sorbose to 2KGA; this chimera showed Enzyme B-type activity. Expression level of above mentioned chimeras was higher than that of wild Enzyme B because it was found that the Enzyme B gene contains many rare codons but Enzyme A does not when the genes were analyzed with the program, Codon Preference (Wisconsin Sequence Analysis Package™, Genetics Computer Group).

(3) Improvement of Codon Usage in Chimera Genes

Figure 4:
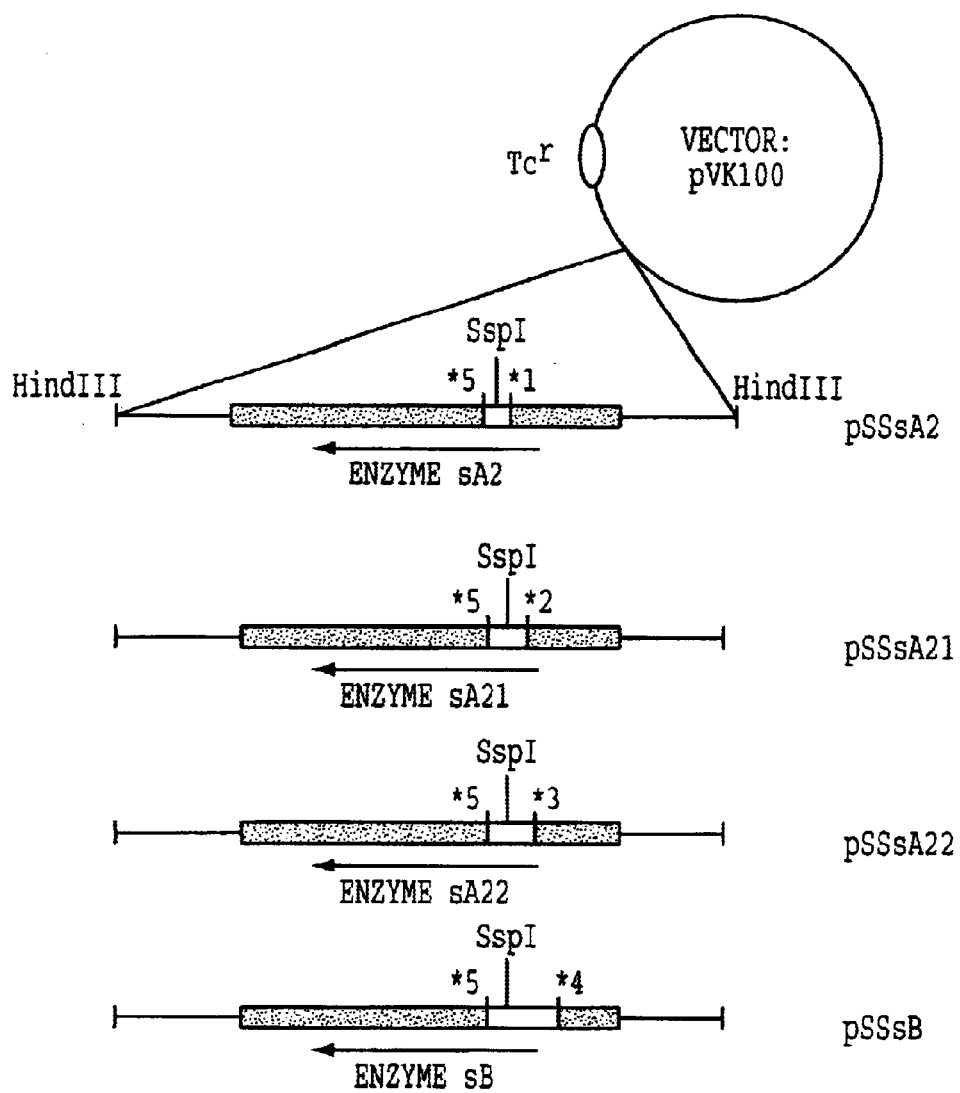
FIG. 4 illustrates the recombinant expression vectors each encoding the chimera Enzyme sA2, Enzyme sA21, Enzyme sA22, or Enzyme sB, using preferable codon usage, wherein these chimeric enzymes have structures denoted by the following particular amino acid residue numbers of the mature amino acid sequences of Enzyme A and Enzyme B: Enzyme sA2 has the structure of Enzyme A amino acid residue Nos. 1–135, Enzyme B amino acid residue Nos. 136–180 and Enzyme A amino acid residue Nos. 180–556; Enzyme sA21 has the structure of Enzyme A amino acid residue Nos. 1–128, Enzyme B amino acid residue Nos. 129–180 and Enzyme A amino acid residue Nos. 180–556; Enzyme sA22 has the structure of Enzyme A amino acid residue Nos. 1–125, Enzyme B amino acid residue Nos. 126–180 and Enzyme A amino acid residue Nos. 180–556; and Enzyme sB has the structure of Enzyme A amino acid residue Nos. 1–95, Enzyme B amino acid residue Nos. 96–180 and Enzyme A amino acid residue Nos. 180–556.

To further improve the chimeras, Enzyme A/B21, Enzyme A/B22, Enzyme A/B25 and Enzyme A/B31 in the view point of the preferable codon usage, the C-terminal two thirds consisting of Enzyme B residues were replaced with the C-terminal two thirds consisting of Enzyme A residues. Enzyme A/B21, Enzyme A/B22, Enzyme A/B25 and Enzyme A/B31 genes were used for constructing new chimera genes of Enzyme sA21 (Enzyme A ammo acid residue Nos. 1–128, Enzyme B amino acid residue Nos. 129–180 and Enzyme A amino acid residue Nos. 180–556), Enzyme sA22 (Enzyme A amino acid residue Nos. 1–125, Enzyme B amino acid residue Nos. 126–180 and Enzyme A amino acid residue Nos. 180–556), Enzyme sA2 (Enzyme A amino acid residue Nos. 1–135, Enzyme B amino acid residue Nos. 136–180 and Enzyme A amino acid residue Nos. 180–556) and Enzyme sB (Enzyme A amino acid residue Nos. 1–95, Enzyme B amino acid residue Nos. 96–180 and Enzyme A amino acid residue Nos. 180–556) (FIG. 4). Actually, the replacement experiments for Enzyme sA2 and Enzyme sB were performed by partially digesting the plasmids, pUC18 carrying Enzyme sA gene and Enzyme B/A1 gene and pUC 18 carrying Enzyme A/B31 gene and Enzyme B/A1 gene with AvaI, ligating the resulting digests, transforming *E. coli* JM109, analyzing the plasmid structure of the transformants by restriction analysis, and determining the nucleotide sequence to confirm the expected recombination site, AvaI. The replacement experiments for Enzyme sA21 and Enzyme sA22 were performed by replacing the HindIII-SspI fragment of pSSsA2 encoding N-terminal part of Enzyme sA2 with the corresponding HindIII-SspI fragment containing recombinated site of Enzyme A/B21 or Enzyme A/B22 gene (FIG. 4).

(4) Kinetic Properties of Chimera Enzymes

Tables 11 and 12 summarizes the kinetic properties of chimera enzymes, Enzyme sA2 and Enzyme sB in comparison with Enzyme A and Enzyme B, respectively.

TABLE 11

Enzyme sA2 vs Enzyme A

|  | Enzyme sA2 | Enzyme A |
| --- | --- | --- |
| $Km_{sorbose}$ | 128 mM | 36 mM |
| $Km_{sorbitol}$ | 2140 | 388 |
| $Km_{glucose}$ | 20 | — |

Products from L-sorbose in product assay with Enzyme sA2 and Enzyme A were 2KGA. Products from D-sorbitol in product assay with Enzyme sA2 and Enzyme A were L-sorbose with trace amount of D-glucose and D-glucose only, respectively. Thus, Enzyme sA2 showed desired characteristics for 2KGA production from D-sorbitol; L-sorbose/L-sorbosone dehydrogenase activity to produce 2KGA from L-sorbose like Enzyme A and D-sorbitol dehydrogenase activity to produce L-sorbose from D-sorbitol like Enzyme B.

TABLE 12

Enzyme sB vs Enzyme B

|  | Enzyme sB | Enzyme B |
| --- | --- | --- |
| $Km_{sorbitol}$ | 61 mM | 128 mM |
| $Ki_{sorbose}$ | 150 | 100 |

In comparison with Enzyme B, Enzyme sB showed higher affinity to D-sorbitol and lower affinity to L-sorbose which is the oxidation product of D-sorbitol and inhibitor in the conversion of D-sorbitol to L-sorbose.

Example 15

2KGA Production from D-sorbitol by GOS2R Derivative Strain Amplified With Chimera AADH Enzymes For evaluating Enzyme sA2 and Enzyme sB, GOBΔK and GOI13 strains were constructed. GOBΔK was made from GOS2R by deleting the whole Enzyme B gene and instead inserting 1.28 kb $Km^r$ gene cassette isolated from pUC4 K [4.1 kb, $Km^r$, $Amp^r$; Pharmacia, Uppsala, Sweden; Viera, J., and Messing, J., Gene 19:259, (1982)] by using a suicide vector pSUP201 [$Amp^r$, $Cm^r$, $mob^+$, a derivative of pBR325, Bio/Technology, 1:784–791, (1983)].

GOI13 was constructed from GOBΔK by replacing wild Enzyme A gene with Enzyme sB gene and deleting wild Enzyme A" gene replaced with gentamicin (Gm) resistant gene cassette with the suicide vector pSUP202 [$Amp^r$, $Cm^r$, $Tc^r$, $mob^+$, a derivative of pBR325, Bio/Technology, 1:784–791, {1983)]. The $Gm^r$ gene cassette was designed to have PstI site at both ends by PCR amplification with the DNA fragment Tn5-GM [Sasagawa et al., Gene 56: 283–288, (1987)] as the template, and the resulting PCR product was inserted into PstI site of pUC4K to produce pUC8 G; $Gm^r$ gene can be isolated from pUC8G by digesting with EcoRI, BamHI, SalI, or PstI.

(1) Effect of Enzyme sA2 Amplification in 2KGA Production

Plasmid pSSsA2, pVK100 with 2.7 kb HindIII cassette containing Enzyme sA2 gene, and its control plasmid pSSA102R, pVK102 with 2.7 kb HindIII cassette containing Enzyme A gene, were introduced into GOI13 by a conjugal mating method as described in Example 6. The resulting transconjugants were cultivated in PMSL10 medium at 30°

C. for 4 days as described in Example 8. GOI13 carrying pSSsA2 and pSSA102R produced 66.3 and 38.5 g/l of 2KGA, respectively, and 8.4 and 25.9 g/l of 2KD (by-product of 2KGA produced from D-sorbitol via D-glucose and D-gluconate), respectively.

(2) Plasmids pSSsA21 and pSSsA22, Which are pVK100 With 2.7 kb HindIII

Cassettes containing Enzyme sA21 and Enzyme sA22 genes, respectively(FIG. 4), were introduced into GOI13 by a conjugal mating method as described in Example 6. The resulting transconjugants were cultivated in PMSL10 medium at at 30° C. for 4 days as described in Example 8. GOI13 carrying pSSsA21 and pSSsA22 produced 66.8 and 77.4 g/l of 2KGA, respectively, and 0.3 and 0.4 g/l of 2KD, respectively.

(3) Effect of Enzyme sB in 2KGA Production

Plasmid pSSsB, pVK100with 2.7 kb HindIII cassette containing Enzyme sB gene (FIG. 4) and its control plasmid pSSB 103R, pVK102 containing 2.3 kb Enzyme B gene, were introduced into GOBΔK by a conjugal mating method. GOBΔK carrying pSSsB, GOBΔK carrying pSSB 103R, and GOBΔK were cultivated in PMSL8 medium as described in Example 8 (2) and produced 52.0, 46.8, and 1.1 g/l of 2KGA, respectively, and 6.9, 9.3, 32.3 g/l of 2KD, respectively.

GOI13, which carries one copy of Enzyme sB on the chromosomal DNA without wild genes of Enzyme B, Enzyme A, and Enzyme A", was also cultivated in PMSL10 medium in 2 days. It produced 79.3 g/l of L-sorbose.

The terms and expressions which have been employed and used herein are terms of description and not of limitation, and there is no intention in the use of such terms and expressions of excluding any equivalents of the features shown and described or portions thereof; it being recognized that various modifications are possible within the scope of the invention.

What is claimed is:

1. An isolated nucleic acid molecule encoding a recombinant polypeptide comprising SEQ ID NO:5 or a polypeptide with at least 80% identity to SEQ ID NO:5, and having alcohol and aldehyde dehydrogenase (AADH) activity.

2. An isolated nucleic acid molecule of claim 1, wherein the nucleic acid molecule is selected from the group consisting of a linear DNA, a circular DNA and an insertion DNA fragment on a chromosome.

3. A recombinant expression vector comprising a DNA sequence selected from the group consisting of SEQ ID NO:1 and DNA sequences which encode a polypeptide with at least 80% identity to SEQ ID NO:5 and having alcohol and aldehyde dehydrogenase activity.

4. A recombinant expression vector comprising a DNA sequence selected from the group consisting of SEQ ID NO:1 and DNA sequences which encode a polypeptide with at least 80% identity to SEQ ID NO:5, wherein the DNA sequence is functionally linked to one or more genetic control sequences and is capable of expression of an enzyme including at least one recombinant polypeptide having alcohol and aldehyde dehydrogenase activity.

5. A recombinant expression vector of claim 4 which is pSSA102R.

6. A host cell transformed with the recombinant expression vector of claim 3.

7. A host cell transformed with the nucleic acid molecule of claim 1.

8. The host cell of claim 6, wherein the host cell is a bacterium.

9. The host cell of claim 6, wherein the host cell is selected from the group consisting of Escherichia coil, Pseudomonas putida, Acetobacter xylinum, Acetobacter pasteurianus, Acetobacter aceti, Acetobacter hansenii, and Gluconobacter oxydans.

10. The host cell of claim 6, wherein the host cell is Gluconobacter oxydans.

11. A process for producing a recombinant enzyme having an alcohol and aldehyde dehydrogenase activity comprising:
   (a) culturing a host cell comprising an expression vector comprising a DNA molecule encoding a recombinant polypeptide having alcohol and aldehyde dehydrogenase activity and amino acid sequence with at least 80% identity to the polypeptide sequence of SEQ ID NO: 5 in an appropriate culture medium; and
   (b) recovering the recombinant enzyme.

12. A process for producing an aldehyde product from a substrate comprising the steps of culturing a host cell of claim 6 in a medium containing the substrate, wherein said substrate is selected from the group consisting of n-propanol, isopropanol, D-sorbitol and D-mannitol, and recovering the aldehyde product.

13. A process for producing a ketone product from a substrate comprising the steps in culturing a host cell of claim 6 in a medium containing the substrate, wherein said substrate is selected from the group consisting of n-propanol, isopropanol, D-sorbitol and D-mannitol, and recovering the ketone product.

14. A process for producing a carboxylic acid product from a substrate comprising the steps of culturing a host cell of claim 6 in a medium containing the substrate, wherein said substrate is selected from the group consisting of L-sorbose, D-glucose, D-fructose and L-sorbosone, and recovering the carboxylic acid product.

15. A process for producing 2-keto-L-gulonic acid from L-sorbose comprising the steps of culturing a host cell of claim 6 in a medium containing L-sorbose and recovering the 2-keto-L-gulonic acid.

16. A process for producing 2-keto-L-gulonic acid from D-sorbitol comprising the steps of culturing a host cell of claim 6 in a medium containing D-sorbitol and recovering the 2-keto-L-gulonic acid.

17. A process for the production of L-ascorbic acid from 2-keto-L-gulonic acid comprising obtaining 2-keto-L-gulonic acid by a process of claim 15 and transforming the 2-keto-L-gulonic acid into L-ascorbic acid.

18. A process for the production of L-ascorbic acid from 2-keto-L-gulonic acid comprising obtaining 2-keto-L-gulonic acid by a process of claim 16 and transforming the 2-keto-L-gulonic acid into L-ascorbic acid.

19. An isolated polynucleotide comprising SEQ ID NO:1.

20. An isolated polynucleotide consisting of a polynucleotide sequence encoding amino acid residues 1 to 95 of SEQ ID NO:5.

21. An isolated polynucleotide consisting of a polynucleotide sequence encoding amino acid residues 1 to 135 of SEQ ID NO:5.

22. A recombinant microorganism comprising expression vector pSSA102R.

23. The host cell according to claim 7 wherein the host cell is selected from the group consisting of a microorganism, a mammalian cell, and a plant cell.

24. An isolated polynucleotide consisting of a polynucleotide sequence encoding amino acid residues 1 to 125 of SEQ ID NO:5.

25. An isolated polynucleotide consisting of a polynucleotide sequence encoding amino acid residues 1 to 128 of SEQ ID NO:5.

26. A recombinant expression vector comprising a polynucleotide sequence according to any one of claims 19–21, 24 and 25.

* * * * *